United States Patent
Damadian et al.

(10) Patent No.: US 7,812,607 B2
(45) Date of Patent: Oct. 12, 2010

(54) MAGNETIC RESONANCE IMAGING SYSTEM, APPARATUS AND ASSOCIATED METHODS

(75) Inventors: Raymond V. Damadian, Woodbury, NY (US); William H. Wahl, Smithtown, NY (US); Hank Hsieh, Berkeley, CA (US); Gordon T. Danby, Wading River, NY (US); John W. Jackson, Shoreham, NY (US); Jevan Damadian, New York, NY (US); Luciano B. Bonanni, Dix Hills, NY (US); Mark Gelbien, Levittown, NY (US); Keith Saboe, Melville, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 12/456,304

(22) Filed: Jun. 15, 2009

(65) Prior Publication Data
US 2009/0256573 A1  Oct. 15, 2009

Related U.S. Application Data

(62) Division of application No. 11/236,184, filed on Sep. 27, 2005, now Pat. No. 7,560,928.

(60) Provisional application No. 60/613,588, filed on Sep. 27, 2004.

(51) Int. Cl.
*G01V 3/00* (2006.01)
(52) U.S. Cl. .................................. 324/318; 324/319
(58) Field of Classification Search ......... 324/300–322; 600/407–445
See application file for complete search history.

(56) References Cited

U.S. PATENT DOCUMENTS

| | | | |
|---|---|---|---|
| 4,651,099 A | 3/1987 | Vinegar et al. |
| 4,675,609 A | 6/1987 | Danby et al. |
| 4,707,663 A | 11/1987 | Minkoff et al. |
| 4,766,378 A | 8/1988 | Danby et al. |
| 4,805,626 A | 2/1989 | DiMassimo et al. |
| 4,829,252 A | 5/1989 | Kaufman |
| 4,924,198 A | 5/1990 | Laskaris |
| 4,968,937 A | 11/1990 | Akgun et al. |

(Continued)

FOREIGN PATENT DOCUMENTS

JP  63-068157  3/1988

(Continued)

*Primary Examiner*—Brij B Shrivastav
(74) *Attorney, Agent, or Firm*—Lerner, David, Littenberg, Krumholz & Mentlik, LLP

(57) ABSTRACT

In one aspect, a magnet comprising a pair of pole supports spaced apart from one another and extending in a generally horizontal direction. The magnet includes a pair of flux return members extending between the pole supports so as to define a frame, each of the flux return members including a first columnar section that extends parallel to the polar axis and a second columnar section that extends perpendicular to the polar axis and projects towards the pole. In another aspect, a magnetic resonance imaging system comprises a ferromagnetic frame that is operative to support an upper pole member and a lower pole member along a vertical polar axis such that a gap is defined between the upper and lower pole members and an access floor that is isolated from the ferromagnetic frame and pole members for providing access to the gap.

10 Claims, 27 Drawing Sheets

U.S. PATENT DOCUMENTS

| | | | |
|---|---|---|---|
| 5,194,810 A | 3/1993 | Breneman et al. | |
| 5,250,901 A | 10/1993 | Kaufman et al. | |
| 5,304,932 A | 4/1994 | Carlson | |
| 5,305,749 A | 4/1994 | Li et al. | |
| 5,317,297 A | 5/1994 | Kaufman et al. | |
| 5,317,298 A | 5/1994 | Dorri et al. | |
| 5,349,956 A | 9/1994 | Bonutti | |
| 5,475,885 A | 12/1995 | Ishikawa | |
| 5,519,372 A | 5/1996 | Palkovich et al. | |
| 5,592,090 A | 1/1997 | Pissanetzky | |
| 5,680,086 A | 10/1997 | Allis et al. | |
| 5,877,665 A | 3/1999 | Obasih et al. | |
| 5,983,424 A | 11/1999 | Naslund et al. | |
| 6,023,165 A | 2/2000 | Damadian et al. | |
| 6,043,653 A | 3/2000 | Takamori et al. | |
| 6,201,394 B1 | 3/2001 | Danby et al. | |
| 6,208,144 B1 | 3/2001 | McGinley et al. | |
| 6,246,239 B1 | 6/2001 | Krogmann et al. | |
| 6,335,623 B1 | 1/2002 | Damadian et al. | |
| 6,346,814 B1 | 2/2002 | Carrozzi et al. | |
| 6,346,816 B1 | 2/2002 | Damadian et al. | |
| 6,369,571 B1 * | 4/2002 | Damadian et al. | 324/318 |
| 6,424,854 B2 | 7/2002 | Hayashi et al. | |
| 6,433,550 B1 | 8/2002 | Kinanen | |
| 6,617,852 B1 * | 9/2003 | Danby et al. | 324/318 |
| 6,621,267 B1 | 9/2003 | Damadian et al. | |
| 6,799,366 B2 | 10/2004 | Tsuda et al. | |
| 6,822,449 B1 | 11/2004 | Bonanni et al. | |
| 6,944,492 B1 | 9/2005 | Persoons et al. | |
| 7,127,802 B1 * | 10/2006 | Damadian et al. | 29/607 |
| 7,525,312 B2 * | 4/2009 | Green et al. | 324/318 |
| 7,560,928 B2 * | 7/2009 | Damadian et al. | 324/318 |
| 2002/0013524 A1 | 1/2002 | Hayashi et al. | |
| 2006/0197530 A1 * | 9/2006 | Damadian et al. | 324/318 |
| 2009/0234222 A1 * | 9/2009 | Green et al. | 600/422 |

FOREIGN PATENT DOCUMENTS

| | | |
|---|---|---|
| JP | 1242056 | 9/1989 |
| JP | 8-050843 | 2/1996 |
| WO | 97/17896 | 5/1997 |

* cited by examiner

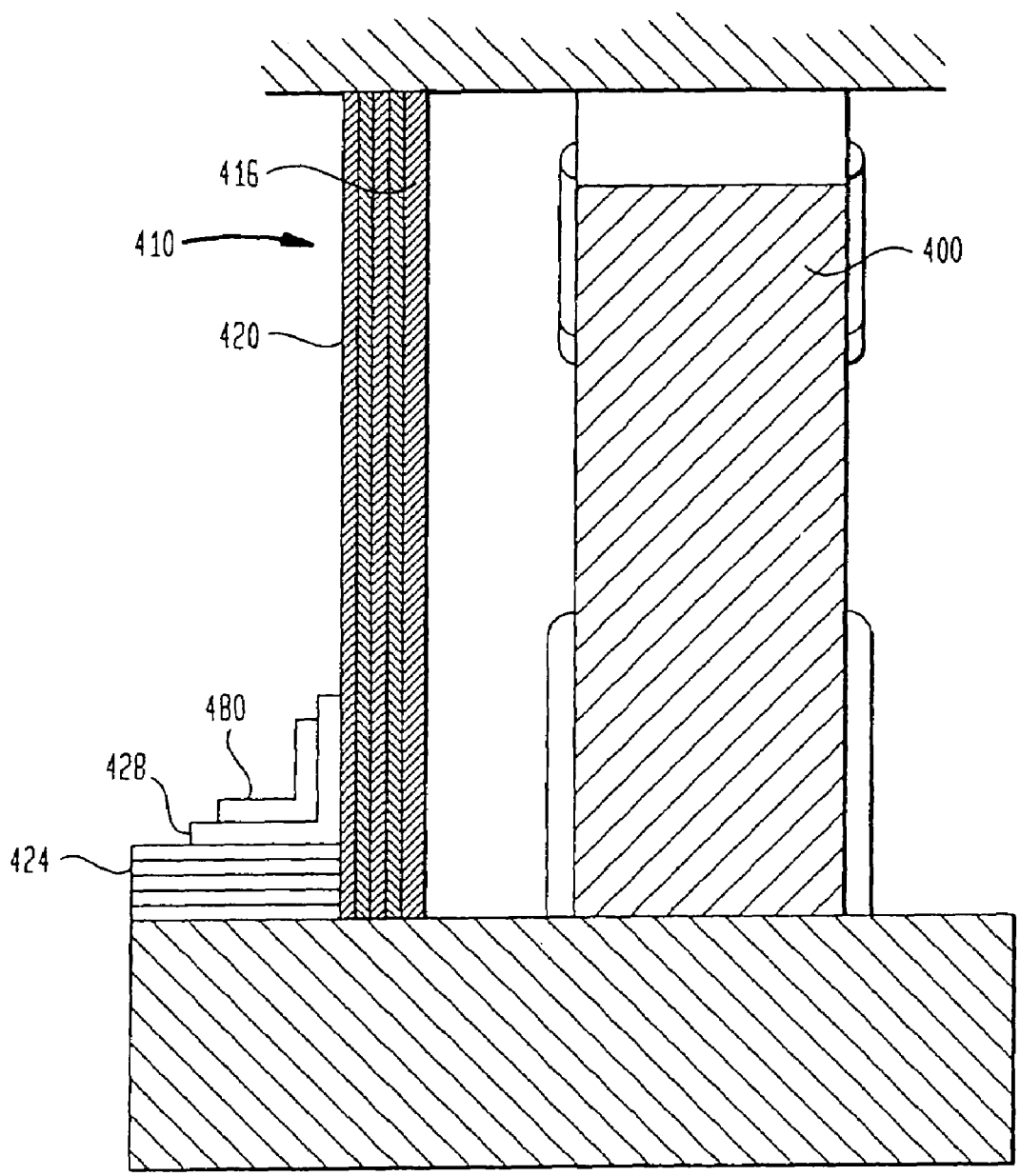

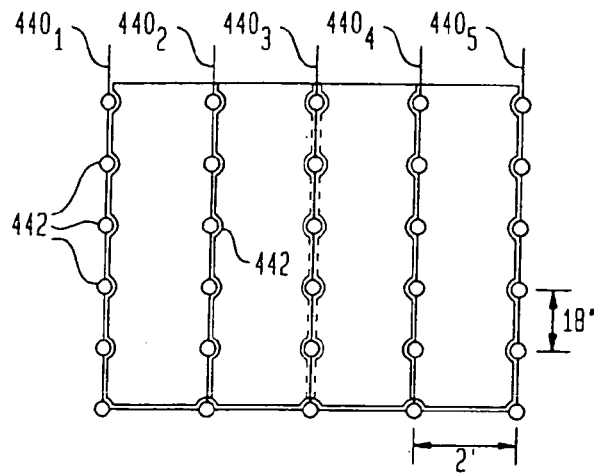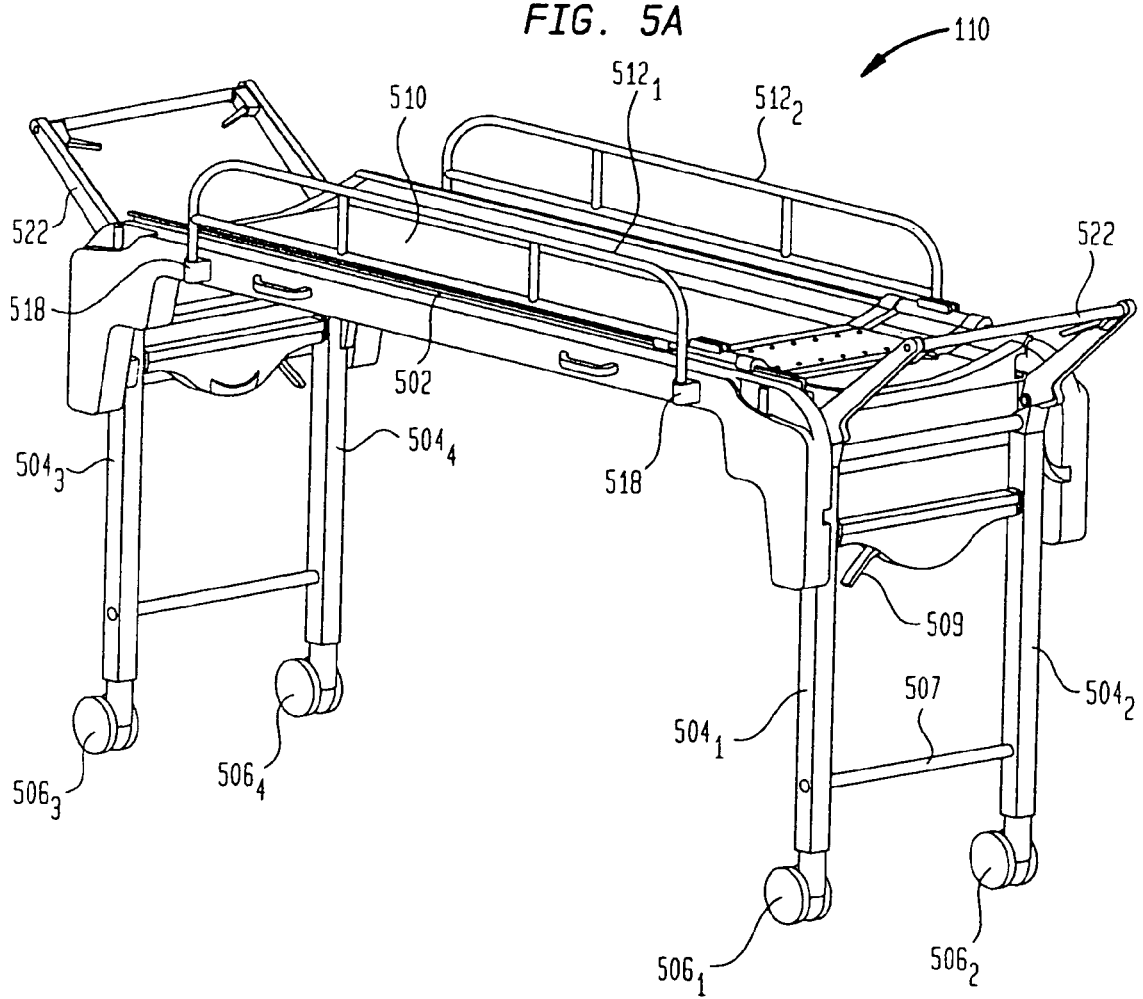

MAGNETIC RESONANCE IMAGING SYSTEM, APPARATUS AND ASSOCIATED METHODS

CROSS-REFERENCE TO RELATED APPLICATIONS

This application is a divisional of U.S. application Ser. No. 11/236,184, filed on Sep. 27, 2005, which claims the benefit of the filing date of U.S. Provisional Application No. 60/613,588, filed Sep. 27, 2004, the disclosures of which are hereby incorporated herein by reference.

BACKGROUND OF THE INVENTION

The present patent application relates to magnetic resonance imaging apparatus and methods for using such apparatus in surgical procedures.

In magnetic resonance imaging, an object to be imaged as, for example, a body of a human subject is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the nuclei to "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are a dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Many conventional magnetic resonance imaging instruments require that a patient lie on a horizontal bed that is then advanced into a tubular bore within a super-conducting solenoidal magnet used to generate the static magnetic field. These units force the patient to undergo an intensely claustrophobic experience while being imaged. Other forms of magnetic resonance imaging apparatus, commonly referred to as "open MRI apparatus," were developed to provide a less claustrophobic experience to the patient and greater access to the patient by medical personnel during the imaging procedure. However, even in this improved apparatus, the patient was still positioned inside the apparatus, and medical personnel attending to the patient would reach into the apparatus from outside, so that components of the apparatus still obstructed access to some extent.

As described in U.S. Pat. Nos. 6,335,623 and 6,541,973, which are assigned to the assignee of the present application, the disclosures of which are hereby incorporated by reference herein, this problem can be solved completely by providing space within the apparatus itself to accommodate medical personnel in addition to the patient. Thus, as shown in certain embodiments disclosed in the '973 and '623 patents, the magnet may include a ferromagnetic frame incorporating a floor, a ceiling and a pair of side walls extending between the floor and the ceiling, a lower ferromagnetic pole structure projecting upwardly from the floor and an upper ferromagnetic pole structure projecting downwardly from the ceiling. The projecting pole structures define a patient-receiving space between them. The magnet also includes flux generating elements such as resistive or superconducting coils or permanent magnets arranged to direct flux through the frame so that the flux passes through the patient-receiving space between the pole structures and returns through the side walls, floor and ceiling. The space between the side walls may be of essentially any size, but is desirably sufficient so that medical personnel can enter into the space along with the patient. In effect, the frame forms a room with a pole structure projecting down from the ceiling and another pole structure projecting up from the floor. The medical personnel inside the room have essentially unobstructed access to the patient from any side. It is, thus, quite practical to perform surgery or other medical procedure on a patient while the patient is in the patient-receiving space of the MRI apparatus. The room defined by the magnet frame may be equipped with features normally found in operating rooms, so that the magnet effectively becomes an MRI-capable operating room. Thus, surgery or other procedures can be performed under MRI guidance.

As shown in detail in the '973 patent, a patient positioning device may include a chassis having a pair of vertically extending end portions or leg portions and a bridge portion extending between these leg portions. The end portions of the chassis are spaced apart by a distance greater than the dimension of the lower pole structure. A bed is movably mounted to the chassis so that the bed can move and pivot in various directions relative to the chassis. The chassis is provided with wheels so that the patient can be positioned in the patient-receiving space of the magnet by placing the patient on the bed and wheeling the chassis into position, with the end portions of chassis disposed on opposite sides of the lower pole structure and with the bridge portion of the chassis spanning across the lower pole structure, so that the bridge portion of the chassis and the bed lie within the patient-receiving space. The patient can then be repositioned in various ways as by turning the bed about a vertical axis, tilting the bed about a horizontal axis or sliding the bed relative to the chassis. These arrangements provide extraordinary versatility in imaging of the patient and in positioning the patient for medical procedures. However, still further improvement would be desirable. For example, the MRI magnet typically is equipped with a false floor covering the ferromagnetic floor. The wheels of the chassis rest on the false floor. Any vibration or movement of the false floor will result in corresponding movement of the patient relative to the magnet. Further, the frame of the magnet must be designed to accommodate the full range of positions and orientations without comprising the susceptibility of the magnet to other sources of vibrations. In addition, the patient positioning device must incorporate mechanical features such as bearings and slides to allow movement of the bed relative to the chassis. It is difficult to accommodate bearings and slides of sufficient strength to allow for all of the desired ranges of movement while still providing a firm, secure support.

The present invention addresses the foregoing needs.

SUMMARY

In one aspect, a magnetic resonance imaging magnet is provided. The magnet comprises a pair of pole supports spaced apart from one another and extending in a generally horizontal direction and a pair of poles, each pole projecting from a respective one of the pole supports along a polar axis that is substantially perpendicular to the horizontal direction so as to define a patient receiving space therebetween. The magnet may further desirably include a pair of flux return members extending between the pole supports so as to define a frame, each of the flux return members including a first columnar section that extends parallel to the polar axis and a second columnar section that extends perpendicular to the polar axis and projects towards the pole.

In accordance with this aspect of the present invention, the pole supports, poles and flux returns are preferably made from ferromagnetic materials. It may be further desirable that these structures be made from low silicon steel or low carbon steel. Most preferably, the poles are made using low silicon steel, whereas the frame is made using low carbon steel.

Further in accordance with this aspect of the present invention, the magnet may further comprise at least two coils, at least one of the coils encircling each of the poles and being operable to provide magnetic flux in the patient receiving space. Further still, the coils may comprise either a resistive electromagnetic coil or a superconducting coil. The superconducting coils may further preferably comprise high temperature $MgB_2$ coils. Further still, the magnetic flux may be generated by a permanent magnet.

Further still in accordance with this aspect of the present invention, the magnet may further desirably include a pair of trusses or support members, each support member supporting one of the flux return members and being mounted on a plurality of vibration isolators. The vibration isolators may comprise air bags, elastomers or hydraulics.

The frame of the magnet may also further be supported on a well structure that includes a pair of support columns that project parallel to the polar axis and defining a well floor between them, and wherein each of the trusses or support members are respectively mounted to the support columns such that the frame of the magnet is isolated from the well floor.

Further in accordance with this aspect of the present invention, the flux return members are positioned apart from each other along the horizontal direction so as to define a work space around the poles of the magnet. Most preferably, the work space is large enough to accommodate a patient with any part of the patient's anatomy located in a imaging volume defined within the patient receiving space In another aspect, the present invention is a magnet for magnetic resonance imaging. The magnet preferably comprises a pair of pole supports spaced apart from one another and extending in a generally horizontal direction; a pair of poles, each pole projecting from a respective one of the pole supports along a polar axis that is substantially perpendicular to the horizontal direction so as to define a patient receiving space therebetween; a pair of flux return members extending between the pole supports so as to define a frame; and a shield member that extends parallel to the horizontal direction and the direction of the polar axis and positioned relative to the frame and poles such that the shield member defines an interior space and an exterior space and wherein a magnetic field strength in the exterior space is substantially less than a magnetic field strength in the interior space. Most preferably, the shield is constructed from a plurality of relatively thin ferromagnetic sheets.

In another aspect, the present invention comprises a magnetic resonance imaging system. The system preferably comprises a ferromagnetic frame that is operative to support an upper pole member and a lower pole member along a vertical polar axis such that a gap is defined between the upper and lower pole members. The frame is preferably mounted to a well that includes a pair of support columns that project parallel to the polar axis so as to define a well floor between them, the ferromagnetic frame being mounted on the support columns. Further in accordance with this aspect of the present invention, the system desirably includes an access floor for providing access to the gap located above the well floor, the access floor being isolated from the ferromagnetic frame and pole members.

Further in accordance with this aspect of the present invention, the ferromagnetic frame is preferably mounted to the well support columns by a pair of support members, each support member being supported on one or more air bags. In addition, the access floor preferably comprises a floor plate mounted to a floor frame, the floor frame being supported by the well floor.

Further in accordance with this aspect of the present invention, the access floor further desirably includes an opening that includes a platform that may be elevated or lowered in a direction parallel to the polar axis and relative to the access floor.

The system may also be desirably equipped with a sensor system for detecting the presence of an object or person on the platform.

In yet another aspect, the present invention comprises a patient positioning system. The system preferably comprises a ferromagnetic frame that is operative to support an upper pole and a lower pole along a vertical polar axis such that a gap is defined between the upper and lower poles; a support frame mounted to the lower pole, the support frame including a pair of support beams extending parallel to each other on opposite sides of the lower pole; and a bed having a frame and a slab, the bed being mounted to the support frame such that each of the support beams engage the frame of the bed.

Further in accordance with this aspect of the present invention, the support is preferably rotatable around the lower pole. In addition, the beams are desirably operable to move the bed over the surface of the pole. Further still, the bed slab is desirably operable to cantilever relative to the lower pole. Most preferably, the frame defines a workspace that can provide access to surgeon to perform MRI guided intervention.

BRIEF DESCRIPTION OF THE DRAWINGS

FIG. 4A is a side view of magnet in accordance with an additional aspect of the present invention.

FIG. 4B illustrates a system for constructing a shield in accordance with an aspect of the present invention.

FIG. 5A is a perspective view of an apparatus in accordance with an additional aspect of the present invention.

DETAILED DESCRIPTION

Figure 1:
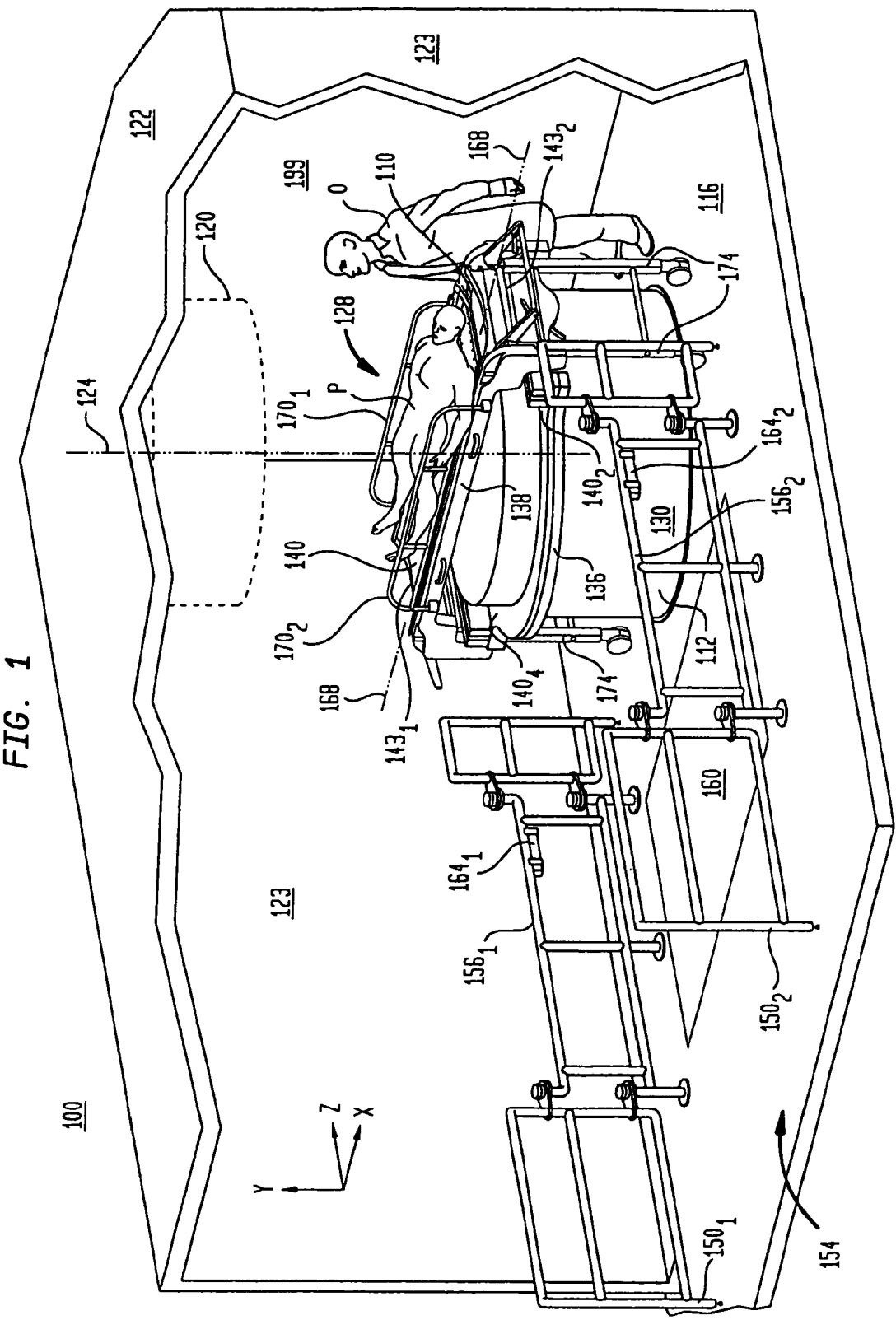
FIG. 1 is a schematic of a magnetic resonance imaging system in accordance with an aspect of the present invention.

Turning now to FIG. 1, there is shown a magnetic resonance imaging system 100 in accordance with an aspect of the present invention. The system 100 includes a magnet 106 and a patient support apparatus 110. The magnet 106 includes a lower magnet pole structure 112 that projects upwardly from a floor 116. As is discussed in greater detail below, the floor 116 is a false floor that is supported by a floor of a well and is isolated from the magnet. The magnet 106 also includes an upper magnet pole structure 120 that projects downwardly from a ceiling 122. For clarity, the upper magnet pole structure 120 is shown schematically in broken lines projecting downwardly through a portion of the ceiling 122. Other structures associated with the magnet are located, beneath floor 116 above the ceiling 122, and behind the side walls depicted 123, but are not shown for clarity. These structures are discussed below. In addition, a front wall (not shown) is also used to house the system in a room, which may serve as an operating theater. The lower and upper pole structures 112, 120 are aligned with each other along a polar axis 124 that generally extends vertically in the y-direction. The upper and lower pole structures 112, 120 are spaced apart so as to define a patient receiving space 128 therebetween. As shown in FIG. 1, a patient P may be positioned within the receiving space 128 using the patient support system 110. Other personnel O may then access the patient P while in patient receiving space 128.

As shown in FIG. 1, the lower pole structure 112 is surrounded by a shroud 130 that is equipped to receive a patient support system 110 that is also included with the system 100. The shroud 130 is equipped with a rotatable frame 136 that included ledges 140 onto which the patient support apparatus 110 may be docked and mounted. When the patient support apparatus 110 is mounted to the frame 136 it may be rotated about the polar axis 124. In addition, the patient support apparatus 110 includes a frame 138 onto which a slab 140 is slidably mounted such that slab 140 is allowed to cantilever relative to the magnet pole. As such, either end of patient support apparatus, 110, may project diagonally outward from the magnet pole and be rotated. This allows any portion of the patient's anatomy to be located in the isocenter of the magnet, i.e., within the center of the imaging volume.

The system 100 further includes a pair of safety gates 150 that are located at the front 154 of the magnet. Each gate 150 is connected to a rail 156, which is mounted to the floor 116. A lift platform 160 forms part of an elevator system, which is located towards the front 154 of the magnet. The rails 156 are equipped with a light gate sensor system 164 that detects the presence or absence of an object, e.g., medical personnel or bed 132, that may be supported by the platform 160. The light gate system 164 works in conjunction with an elevator system to automatically raise the lift platform 160 under certain conditions. In particular, if the lift platform 160 is recessed beneath the floor 116 and the gates 150 are opened, the lift platform 160 is automatically raised to be level with the floor 116, unless a person or object is in the path of the light gate sensors 164.

As an overview, the system 100 operates as follows. A patient is preferably loaded onto the patient support apparatus 110 in a staging area. The patient is then transported through the front 154 and positioned on the platform 160. While on the platform 160, the patient support apparatus is positioned with its longitudinal axis 168 aligned with the y-axis. The patient support apparatus 110 may then be raised to a suitable height such that it clears the lower magnet pole 112. The patient support apparatus 110 is then moved over the magnet pole 112 into the patient receiving space or gap 128. Once properly positioned over the pole 112, the apparatus 110 is then lowered to engage the rotatable frame 136 at ledges 140. With the patient support apparatus 110 mounted onto the frame 136, safety rails 170 and legs 174 are then removed from the patient support apparatus. The patient may then be rotated and translated as discussed above so that the portion of the patient's anatomy to be scanned is located in the magnet's isocenter.

In addition to performing scanning, the system 100 also provides a versatile and open enough environment that can also accommodate one or more medical personnel in addition to the patient. For example, the system may be used in performing a biopsy or other medical procedure. In particular, the space around the poles provides an unobstructed view of a patient supported on the bed 132 in the gap 128. An attendant or medical personnel may have 360° access to the patient from all locations. In addition, the platform 160 may be adjusted so as to accommodate the height of a doctor standing on the platform, who may be performing medical procedures using the images provided by a scan to pinpoint the location of tumors, tissue, bones or organs. In that regard, the system may also include a display (not shown) that is attached to the upper magnet pole so that a surgeon could view images in real time. The magnet design therefore provides an environment that can function as an operating room.

Alternatively, the system may be used to scan patients on an ambulatory or outpatient basis. In that regard, the system allows two or more patient support apparatus to be located in a staging area and used to load patients. When located in the staging area, the legs and wheels of the patient support apparatus are attached to the frame apparatus. In this mode, the patient apparatus is not docket to the lower pole, but is instead used to support and transport the patient to the front of the room housing the magnet. The patients may then be sequentially routed through the magnet 106 thereby improving the throughput of the system 100.

Figure 2A:
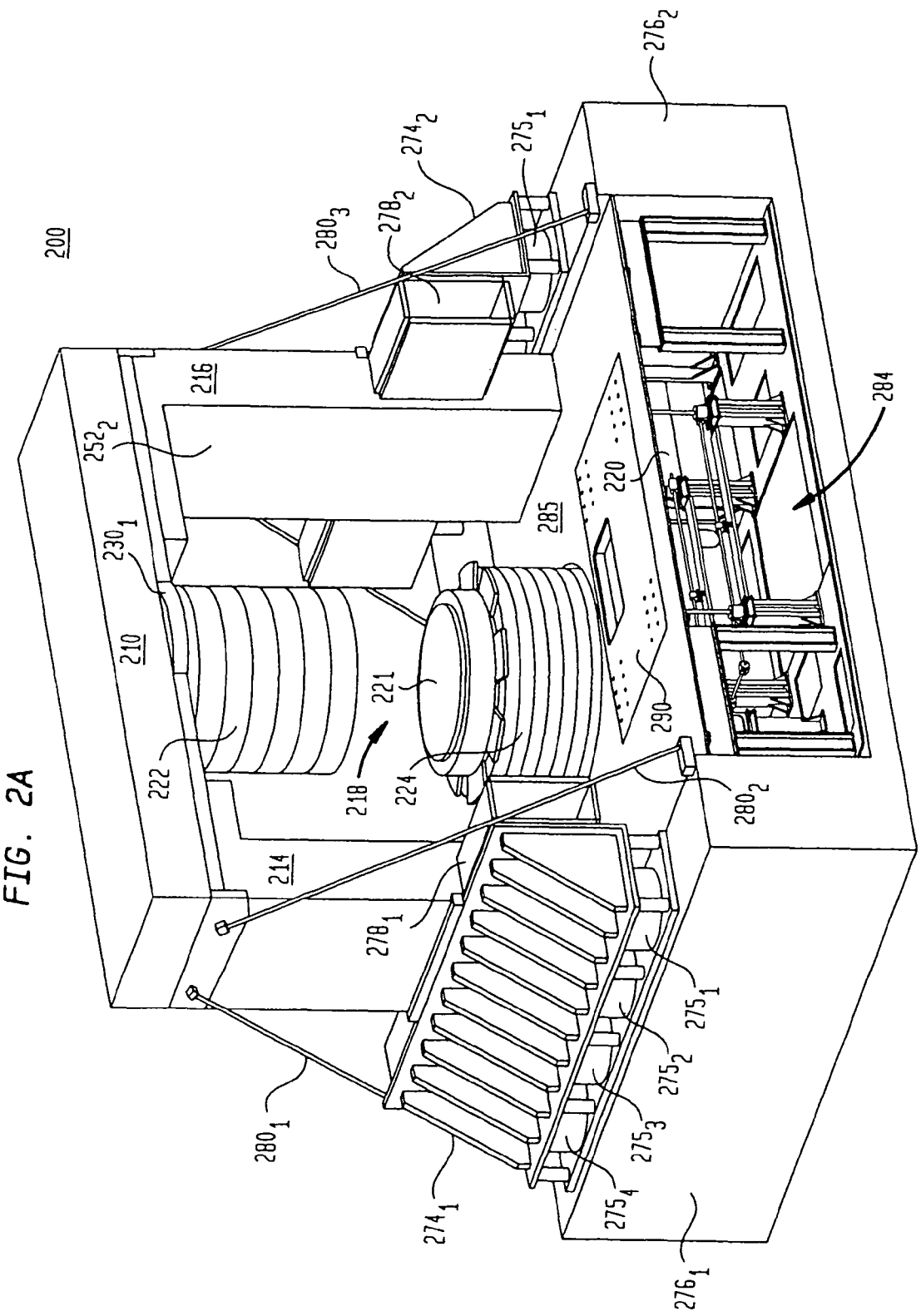
FIG. 2A is a perspective view of a magnetic resonance system in accordance with an aspect of the present invention.
Figure 2B:
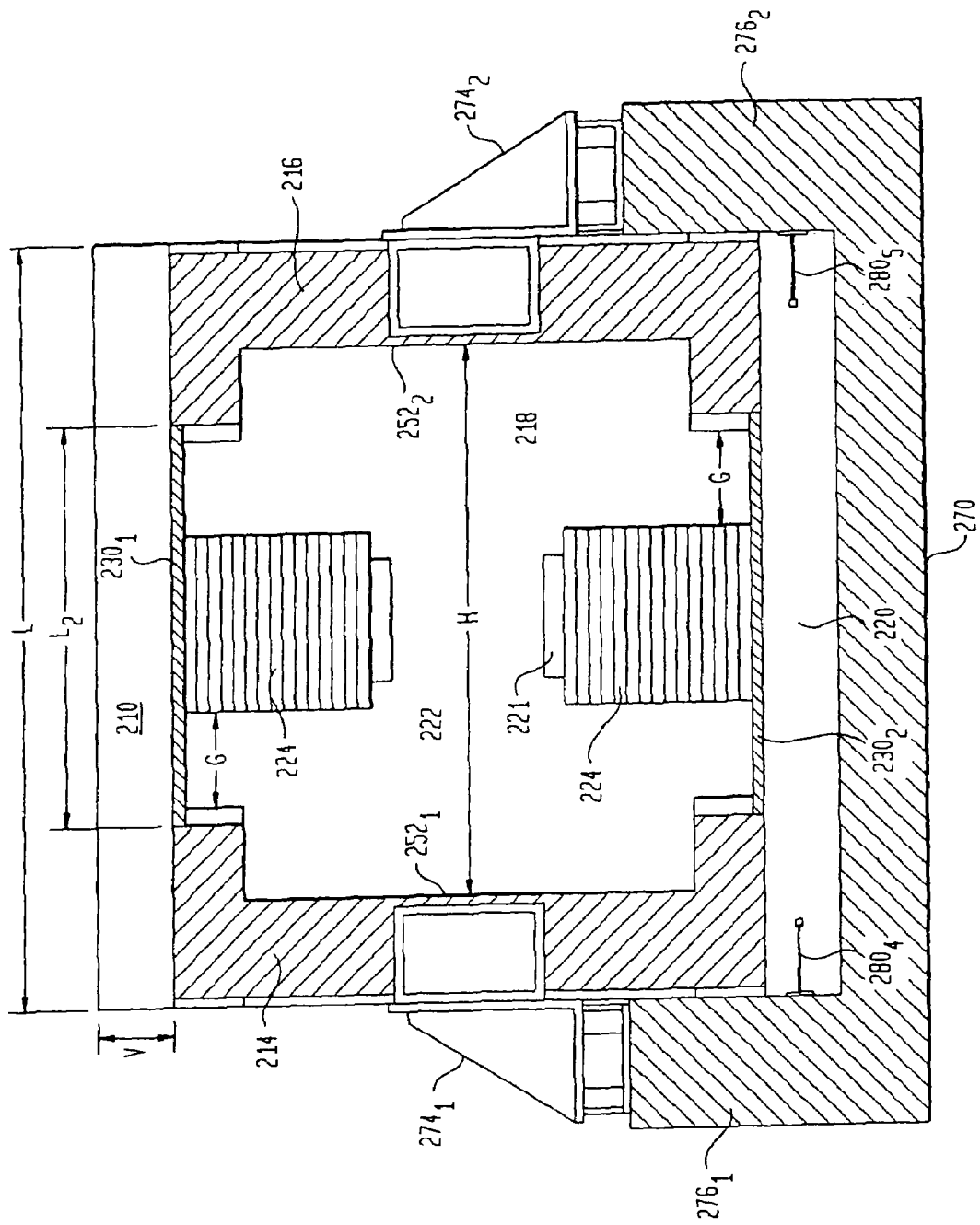
FIG. 2B depicts a front view of the system of FIG. 2A.

Turning now to FIGS. 2A and 2B, there is shown perspective and front views of a magnet 200 that can be used in the system of FIG. 1 in accordance with an aspect of the present invention. In FIGS. 2A and 2B, the shroud, walls and other members that are used to make the magnet structures invisible to a user or patient are removed to reveal the support and other structural details associated with the magnet. In particular, the magnet 200 comprises an upper pole support 210 that extends horizontally across a pair of vertical flux return members 214, 216. A lower pole support 220 is located opposite upper pole support 210 and extends across vertical flux return members 214, 216. The pole supports 210, 220 and flux return members 214, 216 are preferably constructed using a plurality of ferromagnetic plates that are stacked together. As shown, the vertical flux return members 214, 216 are C or U-shaped and include a horizontal run at their respective ends. The ends of flux return numbers 214, 216 preferably terminate approximately two feet away from the magnetic poles in the preferred embodiment. The C-shaped vertical flux return members allows the distance between their inner side walls, which defines the width H of the room housing the magnet, to be wide enough to allow the patient support to cantilever as discussed above, yet while minimizing the length L of the unsupported upper and lower pole supports 210, 220. In particular, the C-shaped members 214, 216 can be moved closer together than a vertical columnar structure would allow. This reduces the length L, which reduces the vibration of the poles, e.g., up and down, due to supports 210, 220. More particularly, the distance L2 is preferably selected to be of a length that avoids mechanical vibration without providing a path for flux to leak from the pole into the vertical flux return members without going through the upper or lower pole support, which also functions as a flux return path or member. Put another way, L2 must be chosen to prevent leakage across the gap G. In a preferred embodiment, H is approximately 160 inches and the vertical dimension V of the pole supports is approximately 16 inches.

The upper and lower pole supports and vertical flux return members define a frame or yoke that provides a magnetic circuit path for flux that is transported across a patient receiving space 218 between the lower pole 221 and an upper pole 222. The magnetic flux is developed by a coil 224 that is shown encircling only lower pole 221 in FIG. 2A. A coil similar to that shown on pole 221 would also encircle upper pole 222 when the magnet is fully assembled. The coil 224 may comprise stacked layers of conductor turns that define a resistive electromagnet. The conductor turns may be aluminum or copper insulated by fiberglass tape. A cooling system is associated with the coils and may comprise any cooling system known in the art.

Figure 2C:
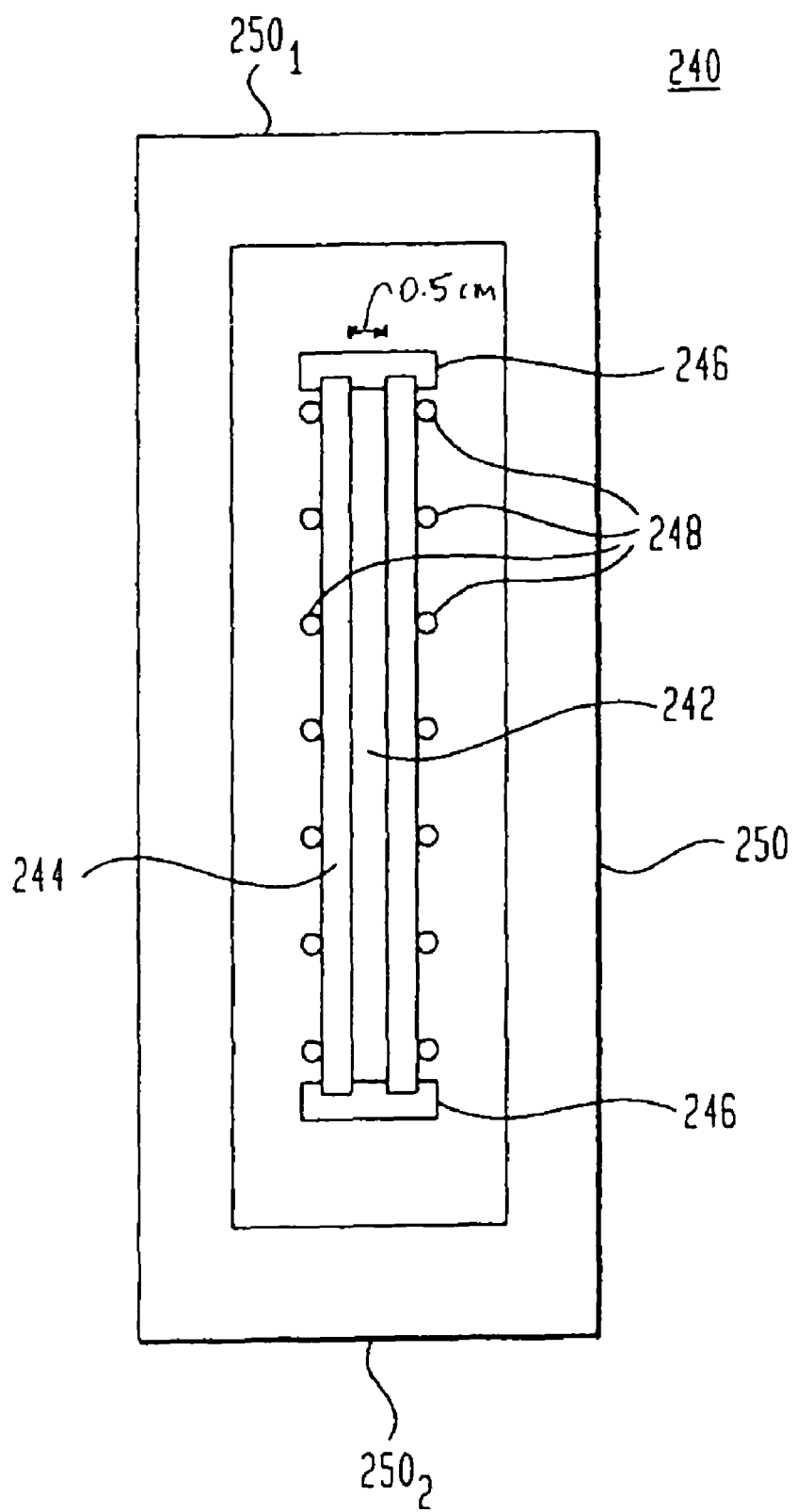
FIG. 2C illustrates a superconducting coil assembly cross-section in accordance with an additional aspect of the present invention.

The resistive electromagnetic coil may be replaced by a conventional or high temperature superconducting coils. Superconducting coils are typically enclosed in vessels referred to as cryostats filled with a coolant such as liquid helium for conventional low temperature superconductors such as NbTi or Nb$_3$Sn or, preferably, liquid nitrogen for high temperature superconductors. The coolant maintains coils at temperature low enough to provide superconductivity. The required temperature depends upon the composition of the superconducting material. The superconducting coils in their cryostats surround the poles in approximately the same position as resistive coils 224. FIG. 2C illustrates a cross-sectional view of a high temperature coil assembly 240 that may be used with magnet 200 in accordance with an additional aspect of the present invention. The high temperature coils may comprise MgB$_2$ coils or other high temperature coils. The coil assembly 240 includes a superconducting winding 242 arranged between coil support 244. The coil supports 244 are capped using end caps 246. Cooling tubes 248 are shown encircling coil support 244 and may include a gas at 15 degrees Kelvin such as provided by a cryo-cooler. The windings, coil supports, cooling tubes and other support structures are preferably housed in a vacuum box 250. In the embodiment shown in FIG. 2C, the coil winding 242 extends approximately 12 centimeters between the end caps 246 and is approximately 0.5 centimeters thick. The box 250 is approximately 17 centimeters between its edges ($250_1$ and $250_2$). The box is approximately 6 centimeters in width.

In addition to the electromagnets and superconducting coil assembly described and shown, the flux generating means may comprise permanent magnet material, which is preferably concentrated beneath the poles.

Returning to FIGS. 2A and 2B, the upper pole 222 is shown without coils that would normally likewise encircle it so as to reveal additional details associated with the construction of the poles. In particular, and as seen with respect to upper pole 222, in the preferred embodiment each pole is generally cylindrical in shape and formed by stacking a plurality of circular ferromagnetic plates together to form pole stems. Each pole stem is connected to its respective support member using a base plate 230. The lower pole 221 is preferably 4 to 7 feet across in diameter. In the preferred embodiment, the lower pole is 52 inches in diameter. Where the pole is of a smaller diameter it may be elongated along its polar axis to obtain the field strength needed with additional ampere turns.

As seen in FIGS. 2A and 2B, the lower pole support 220 is positioned within a U-shaped well 270. A pair of support members 274 is mounted via a plurality of air bags 275 atop vertical columns 276 that form part of the well 270. The support members 274 may comprise trusses or gussets that function to support the frame as shown. The trusses 274 are each connected to the vertical flux return members 214, 216 via arms $278_1$, $278_2$, respectively. The trusses and air bags provide protection against vibration that may be caused by the surrounding environment. In addition, although in the preferred embodiment, the support members are mounted over air bags, other types of vibration isolators may be used in place of air bags. For examples, elastomers or hydraulics may be used to provide vibration isolation. The magnet 200 may be further secured by sway linkages 280 that provide additional protection against vibration.

Figure 2D:
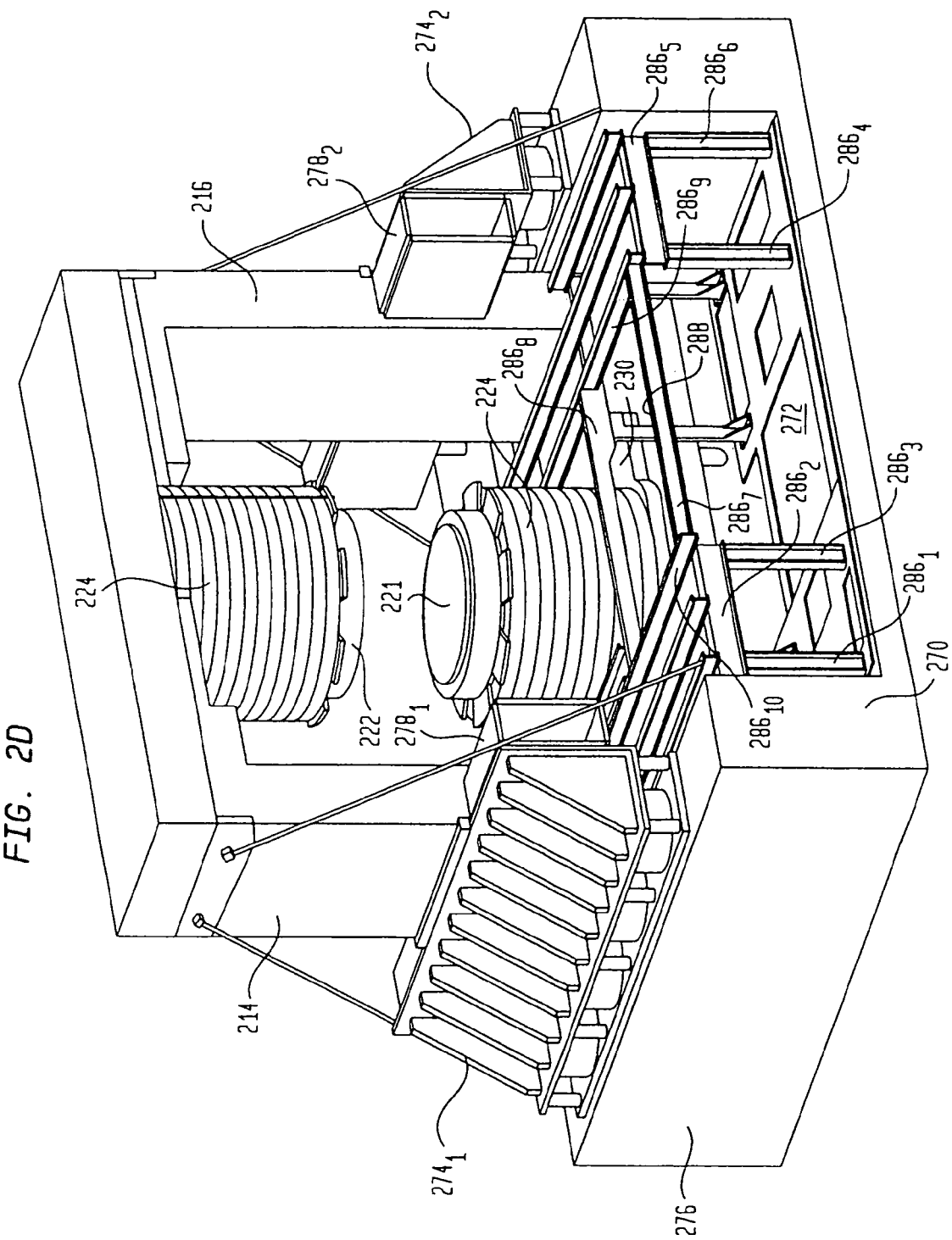
FIG. 2D depicts a perspective view of the system of FIG. 2A.

As best seen in FIGS. 2A and 2D, a land bridge 284 is supported above the floor 272 of the well 270. The land bridge 284 comprises a floor plate 285 that is mounted to a support frame. As shown in FIG. 2D, the support frame comprises a plurality of vertical and horizontal support members 286. The support members $286_7$ through $286_{10}$ are arranged to provide an opening 288 for a lift platform 290. The support frame includes additional openings through which the lower magnet pole 221 and vertical flux return members 214, 216 are inserted. This arrangement allows the land bridge 284 and floor plate 285 to float relative to the magnet 200 or vice versa. More particularly, the magnet frame (structures 210, 214, 216 and 220) and poles 221, 222 are supported by the trusses 274, which are supported by the air bags 275. The air bags 275 protect against horizontal and vertical vibrations. As the land bridge is not supported by the air bags 275, vibrations that may be caused by a person walking across the land bridge are not coupled to magnet 200. In this way, such vibrations do not affect the imaging process. This ultimately leads to a reduction to the number of times a patient needs to be scanned, which increases scanning throughput.

Figure 3A:
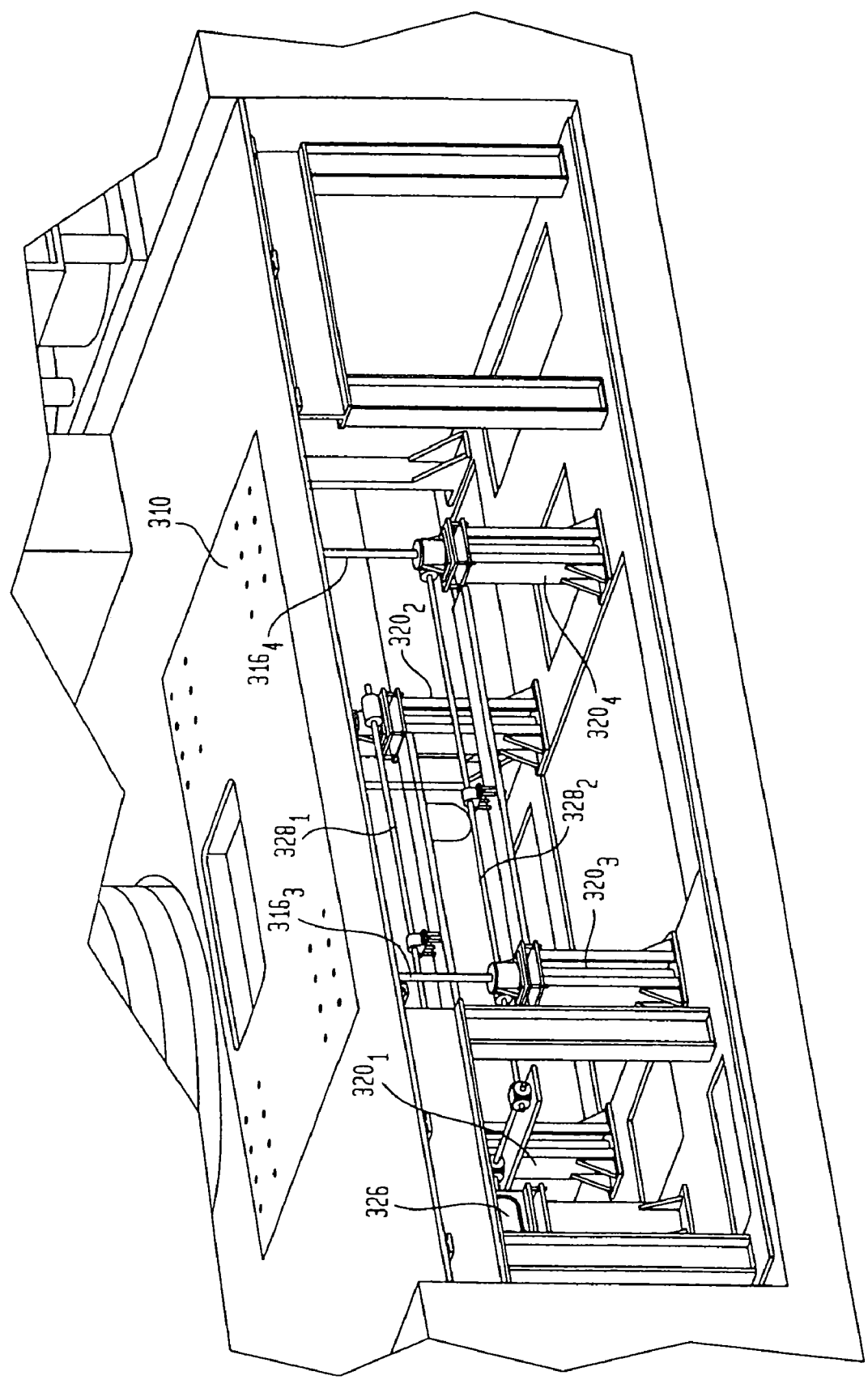
FIG. 3A is a perspective view of a portion of a magnet floor in accordance with an aspect of the present invention.
Figure 3B:
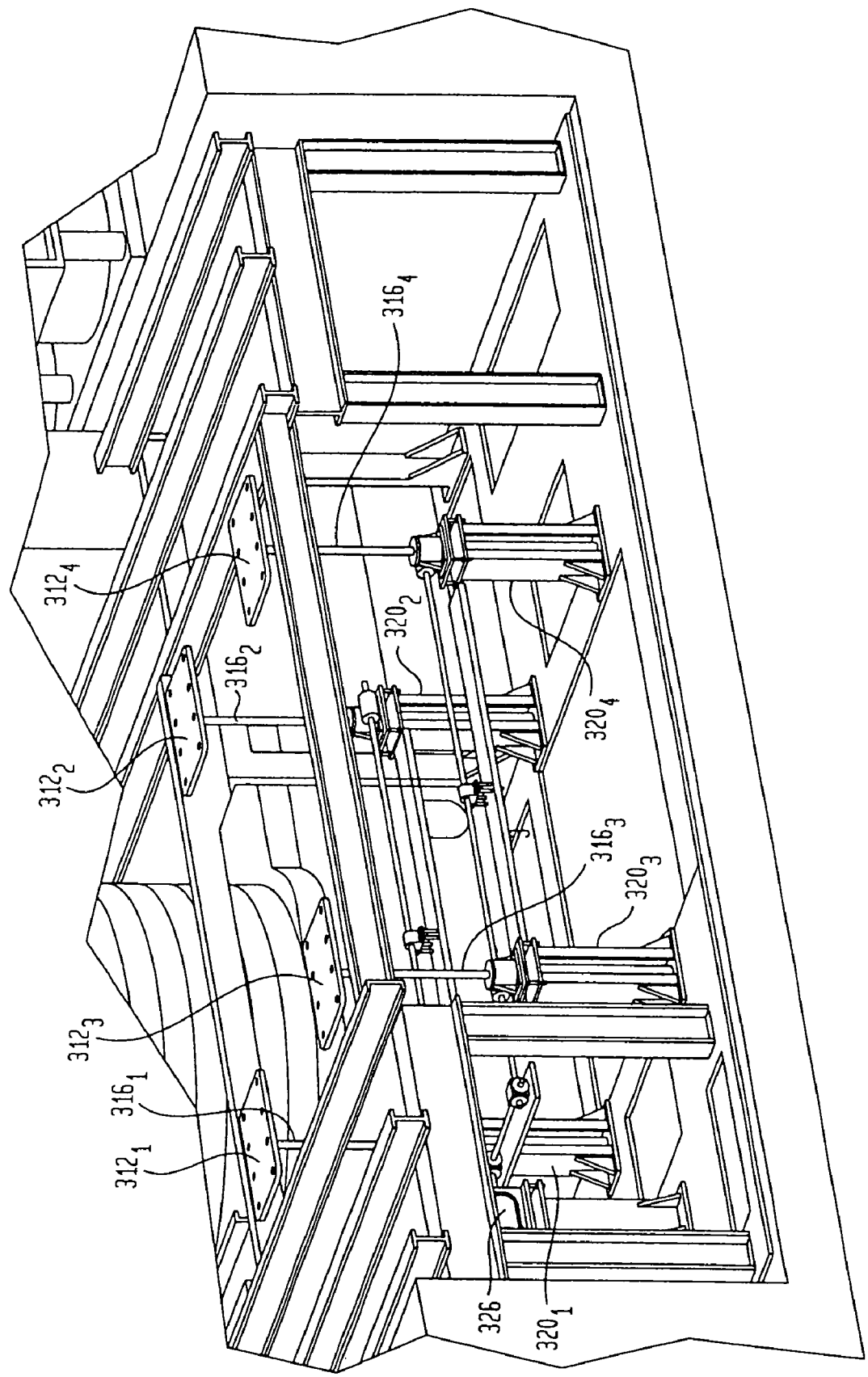
FIG. 3B is an exploded view of FIG. 3A.

Turning now to FIGS. 3A and 3B, there is shown an arrangement of an elevator system 300 in accordance with an aspect of the present invention. The system 300 comprises a lift platform 310, which is mounted to four support stands 312. The support stands 312 are mounted to respective screw jack rods 316. Each rod 316 is threaded into a jack 320. The jacks 320 are connected to electric motor 326 via a pair of rods 328. In operation, the motor 326 rotates rods 326, which results in the support stands being lowered or raised depending on the rotation direction. As discussed above, the elevator allows the height of a surgeon to be adjusted relative to the height of patient support when the patient support is mounted to the lower magnet pole. Such height adjustments aid in allowing a surgeon to more comfortably perform a surgical procedure. The lift may also be used for patient loading. For example, the lift may be used to lower the patient support apparatus or bed to a height that is more suitable to loading a patient in a wheel chair. After the wheel-chaired patient is loaded onto the bed, the lift is then raised to be level with the floor and the bed is docked and mounted as described in further detail below.

In addition to the structures discussed above, the magnet assembly in some circumstances may require localized shielding. For example, where the room housing the magnet needs to be of a depth that accommodates rotation around the lower pole with the bed cantilevered such that either a patient's head or feet is positioned in the imaging volume, localized shielding may be required to prevent leakage towards, for example, the rear of the magnet (see FIG. 1, back wall 199). Although magnets made using ferromagnetic materials, as discussed for example in relation to FIGS. 1 and 2, tend to have localized fields, leakage may occur into the electronics and other equipment that is needed to operate the magnet and other accessory equipment. In the embodiment of FIG. 1, such electronics and equipment may be conveniently placed adjacent the rear wall 199 outside the room.

FIG. 4A shows a side view of a magnet 400 that includes a localized shield 410. As shown, the shield 410 is located behind back wall 416. As best seen in the exploded view of FIG. 4B, the shield 410 comprises a vertical member 420 and a horizontal member 424. The shield 410 also includes a corner sheet 428 and an angle iron 430.

The shield 410 may be constructed using four foot wide transformer sheets. As best seen in FIG. 4B, support struts 440 spaced 2 feet apart are secured to the scanner wall. Studs 442 cut from threaded rods are welded to the support struts 440 with a spacing of approximately 18 inches between studs. Clearance holes are punched in the transformer sheets permitting sheets to be slid onto the studs 442. Holes are also punched along the edges of the transformer sheets to clear studs which are 2 feet away from the centerline of the transformer sheets. The sheets are then slid over the studs in an overlapping pattern as follows: sheet 1 is centered over the studs along strut $440_2$; sheet 2 is centered over the studs along strut $440_4$; and sheet 3 is overlaid over sheets 1 and 2 by centering it over the studs along strut 4403. The pattern is repeated to extend beyond the sides of the magnet (length L in FIG. 2B) as required and to a thickness that prevents magnet flux leakage into the space beyond the shield wall. In a preferred embodiment, the rear vertical shield wall may employ 40 layers of 25 thousands thick M19 sheets which are 10 feet long (vertical direction). The horizontal section of the floor had 4 foot wide sheets of M19 placed above the floor at right angles to the vertical shield wall. Coupling between the horizontal and vertical shields are enhanced with 2 feet wide transformer sheets bent at 90° at their longitudinal centerline, i.e., ±1 foot on each side of the bend.

While the shield wall described above can be built up as described above, it may be easier to place multiple sheets over the studs at the same time at each location. When the outermost bundle edges butt up against each other, small straps secured to the studs assist in ensuring contact between the layers. The shielding described above has been shown to reduce flux leakage to earth field levels of about 0.5 Gauss immediately outside the magnet enclosure. This allows power supplies and other equipment behind the back wall to be shielded and obviates the need to warn operators and other staff that may be operating such equipment.

Turning now to FIG. 5A, there is shown a perspective view of a patient support apparatus 110 in accordance with an additional aspect of the present invention. The patient support apparatus or bed 110 may be considered as having three modes of operation or configuration: (1) gurney mode; (2) docking mode; and (3) pole mounted. Each of these modes will be described in detail below.

The bed 110 comprises a frame 502 which is supported by four detachable legs 504. Each leg 504 includes a caster 506 that allows the bed 110 to be used to transport a patient from a staging area for imaging or a medical procedure, which we conveniently refer to as the gurney mode. The bed 110 also includes a slab 510 that is mounted to the frame 502 within a track that allows the slab to cantilever relative to the frame. The bed 132 also includes safety rails 512 which are mounted into openings 518 provided along the longitudinal edges of the frame 502. The rails 512 are designed to fold inward when pressure is applied from outside the bed, but provides full support for the patient from within the bed frame. Control handles 522 are mounted to each end of the frame and, as is discussed in further detail below, are used to dock and mount the bed to the rotatable frame.

Figure 5B:
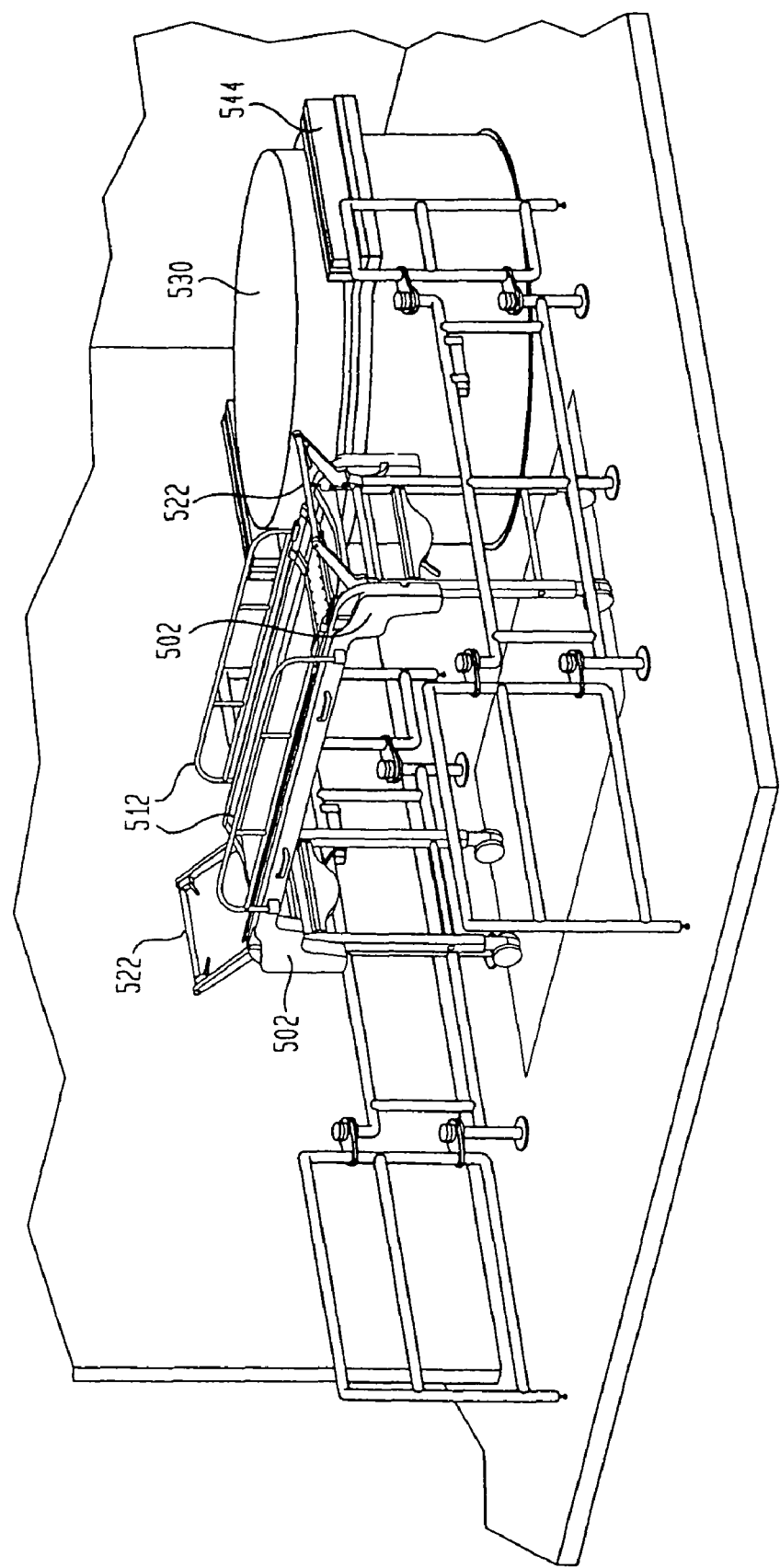
FIG. 5B is perspective view of a system in accordance with an aspect of the present invention.
Figure 5C:
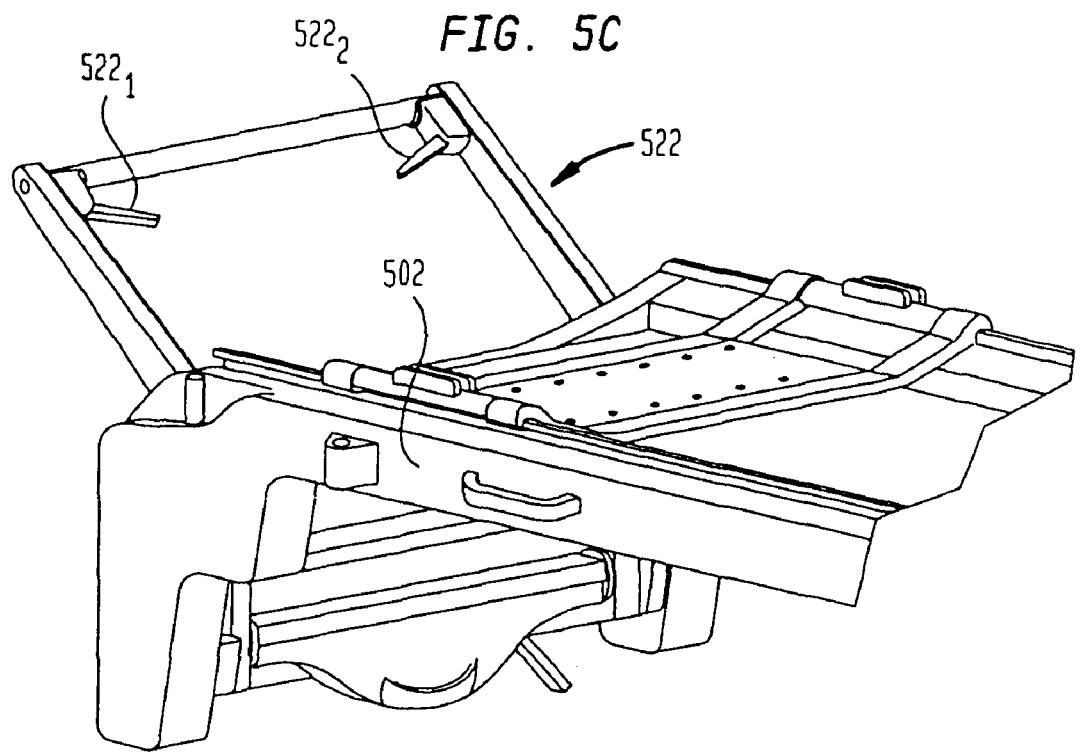
FIG. 5C illustrates a portion of the apparatus of FIG. 5A.
Figure 5D:
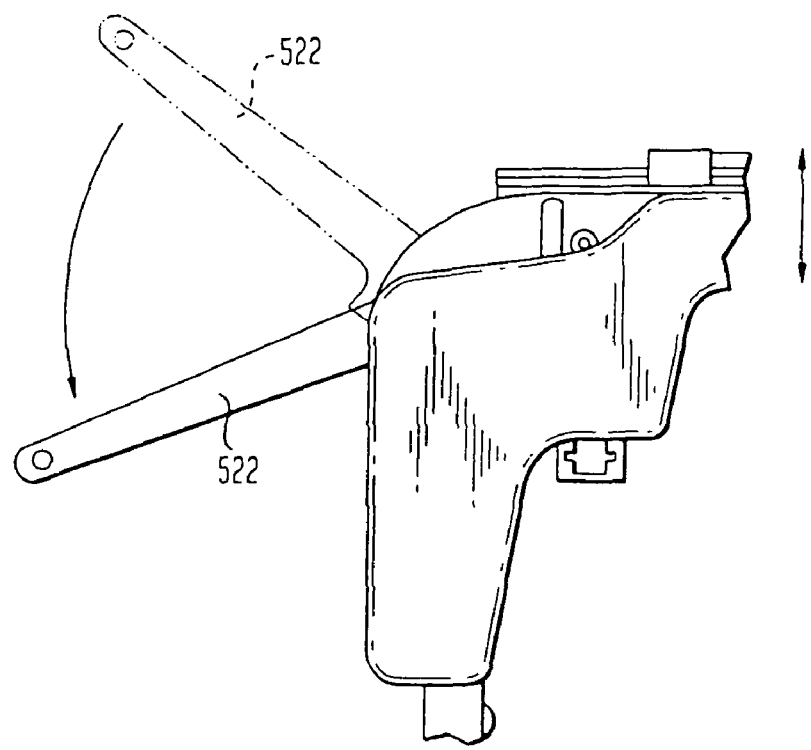
FIG. 5D illustrates a portion of the system of FIG. 5B.

In particular, after a patient is loaded onto the bed, the bed 110 is then moved next to lower magnet pole 530 as is shown in FIG. 5B and prepared to be docked to the magnet pole 530. The bed rails 512 are preferably first removed from the frame 502 before the bed is mounted, but may also be removed after the bed 110 is mounted to the rotatable frame. Next, the bed frame is raised to its docking position by lowering the handles 522. As best seen in FIGS. 5C and 5D, the handle 522 is equipped with a pair of levers 5221, 5222 that unlocks the handle 522 allowing it to be lowered, thereby causing the frame 502 and slab 510 to be raised. When the handle reaches the docking position it preferably locks into place to prevent any further unwanted lowering or raising of the bed 110.

Figure 5E:
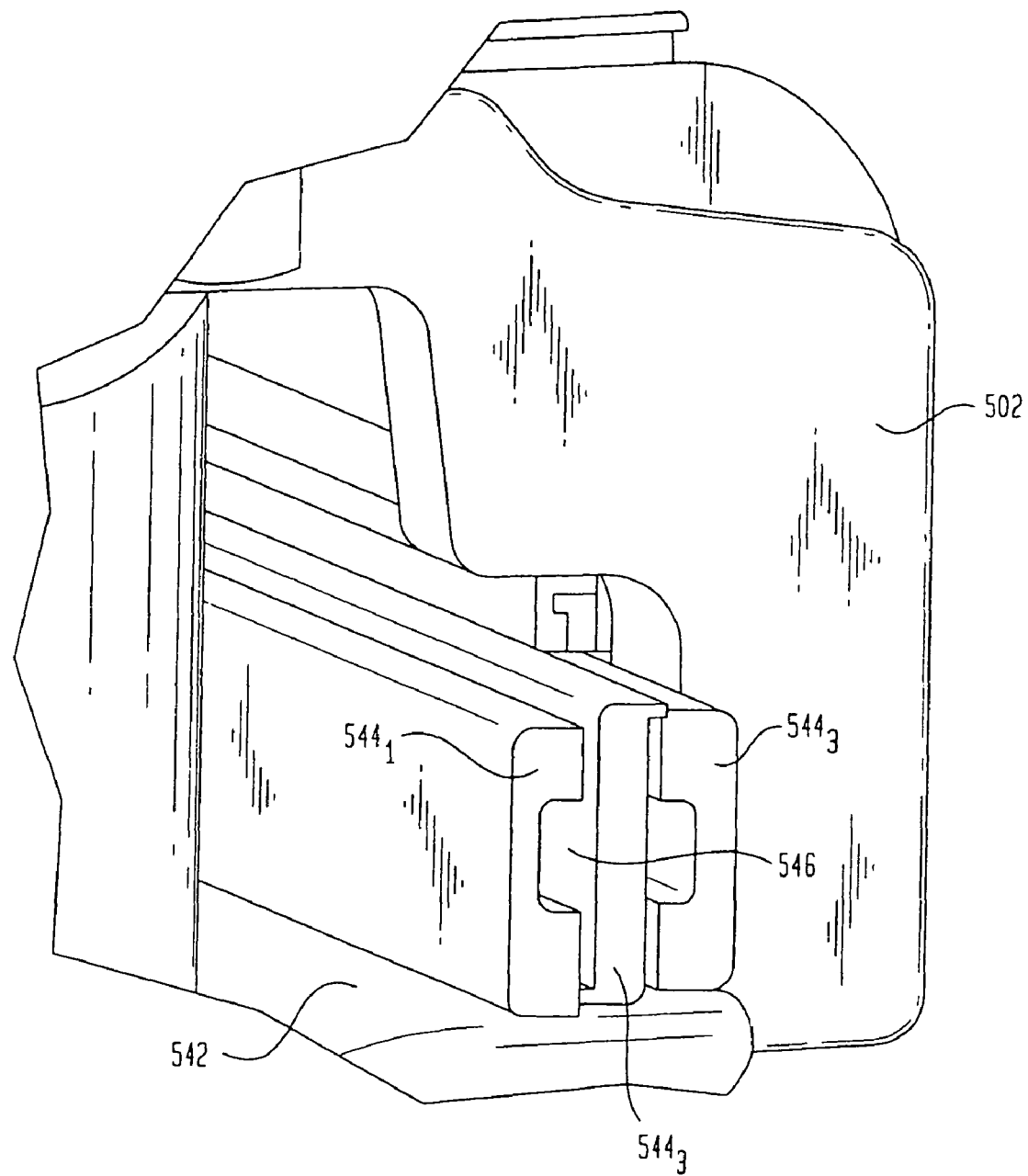
FIG. 5E is an exploded view of a portion of the apparatus of FIG. 5A.

As best seen in FIG. 5E and FIG. 1, the bed 110 is then moved over the pole 530, so that frame 502 is positioned over the rotation frame 538 mounted on the magnet shroud 540 at ledges 542, which extend parallel to each other on opposite sides of the pole. A mounting beam 544 is secured at each ledge 542. The beam 544 includes an inner base member 544 that is affixed to the mounting ledge 542. A middle member 544 is slidably mounted into an opening 546 on the base member 544. The opening 546 provides a track on which the middle member slides relative to the base member 544. An outer member 544 is likewise slidably mounted on the middle member. Once the bed docks onto the rotation frame 538, the bed 132 is slid towards the center of the magnet over the beam 544. With the bed 132 centered on the magnet pole 530, the handles 522 are then raised to their upright position causing the bed frame 502 to be lowered onto the beam 544 and rotation frame 538. In this position, the entire weight of the bed is then supported by the rotation frame 538.

Figure 6:
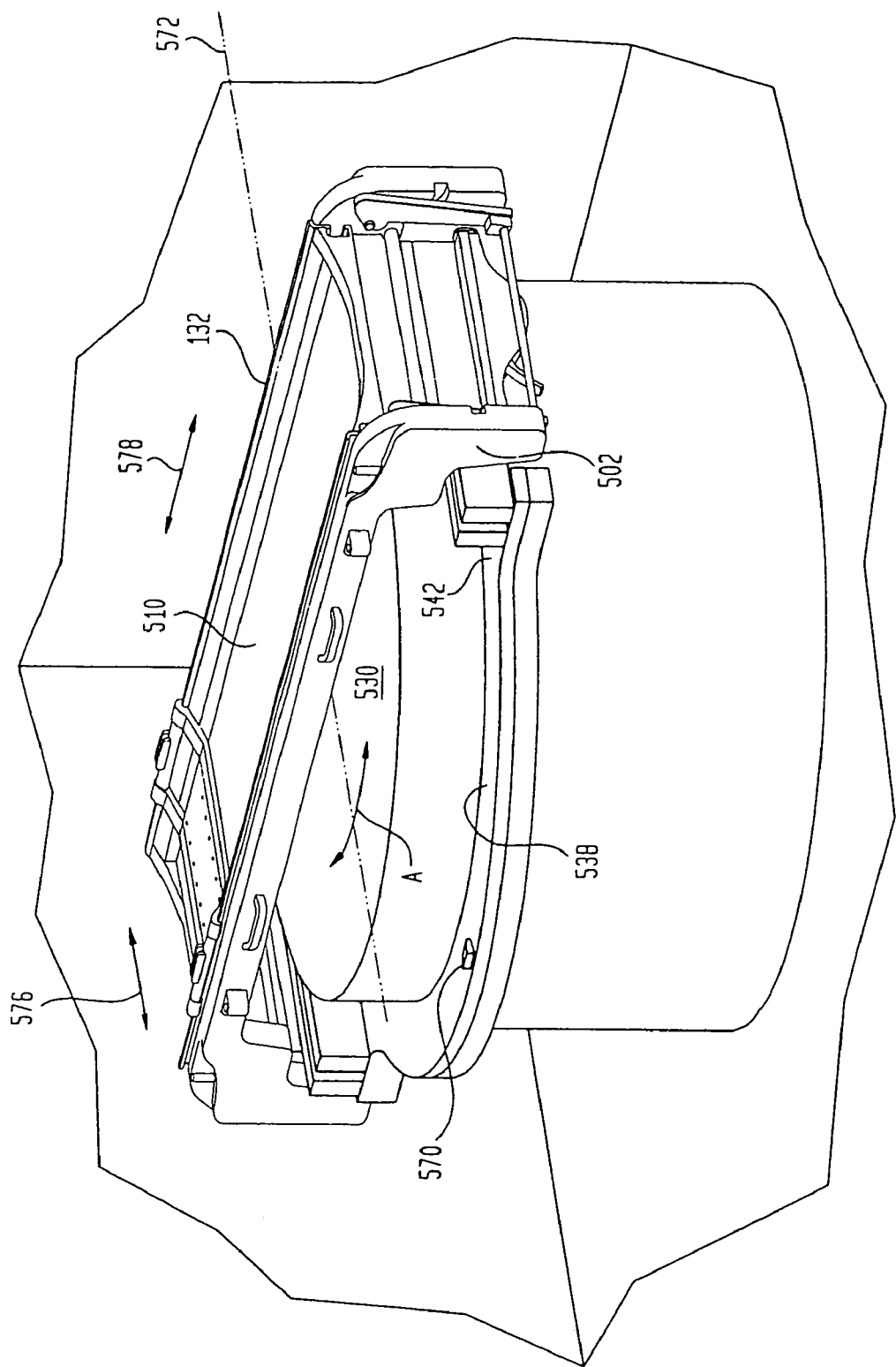
FIG. 6 illustrates a patient positioning system in accordance with an aspect of the present invention.

With the bed 110 mounted to the frame 502, the legs 504 may then be preferably removed. In the preferred embodiment, the legs are removed by grasping bar 507 and rotating it upward 90° and away from the magnet pole. A lever 509 is then used to release the legs from the frame. FIG. 6 shows the bed 132 after it is mounted to the pole 530 and the legs have been removed. The legs 504 may include sensors that detect the presence of a load on the legs and prevent the legs from being removed from the bed frame.

As illustrated in FIG. 6, once the bed is mounted onto the pole 530, or more particularly to rotation frame 538 at ledge 542, it may then be rotated around the pole as is depicted by arrows A. As an additional safety feature, the rotation frame 538 is equipped with one or more stops 570 that allow the bed 132 to be docked at 0° of rotation as shown in FIG. 6, or 90° of rotation (line 572) on the stop 570 shown. Note, however, that the bed 110 may rotate 360° about the polar axis. In addition to rotation about the pole 530, the bed 110 may slide side-to-side along direction 576. The slab of the bed may also cantilever on the beam 544 along the direction 578. As discussed above, the members that comprise the beams are slidably relatively to each other along the ledge 542. This additional adjustment allows for greater flexibility with respect to bringing a patient close to a doctor, who is standing at the edge of the pole.

Figure 7:
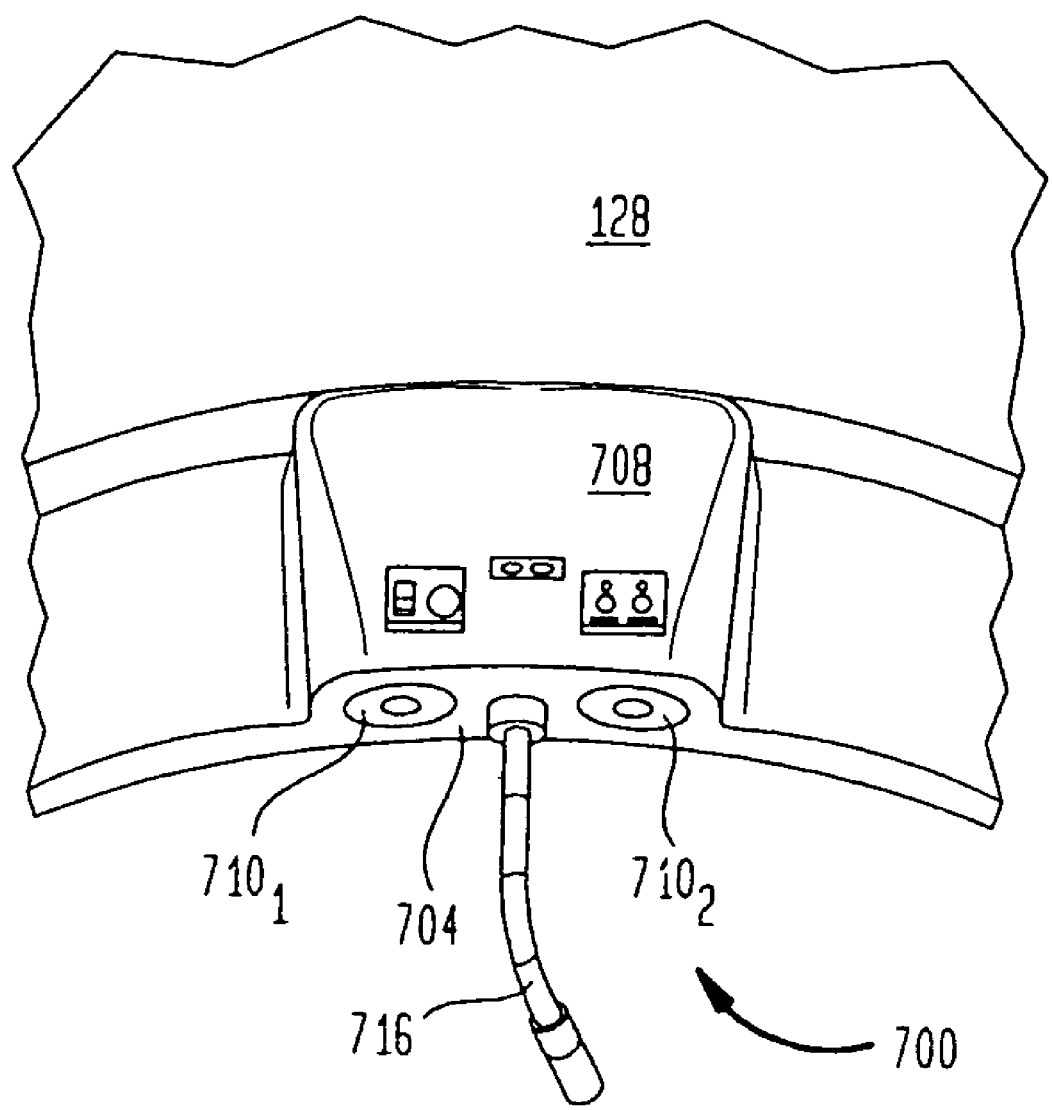
FIG. 7 illustrates a lighting system in accordance with an aspect of the present invention.

Turning now to FIG. 7, there is shown a lighting configuration 700 in accordance with an additional aspect of the present invention. The lighting configuration 700 is desirably mounted to the upper magnet pole, e.g., pole 124 in FIG. 1, and is used to light the magnet gap 128. As shown, the lighting configuration 700 includes a fixture 704 that is mounted onto a canopy pod 708. The fixture 704 includes lamps 710 that provide ambient lighting. The lamps preferably comprise LED lights, which can be tilted within their fixture 704 from straight down to close to the center of the magnet. The fixture also includes a receptacle for a "goose neck" directional lamp 716. The lamp 716 may be tilted towards the center of the magnet and provide lighting that is particularly focused on a portion of a patient's anatomy during a surgical procedure. In addition, in the preferred embodiment, the lamp is detachably mounted to the fixture 704.

Figure 8:
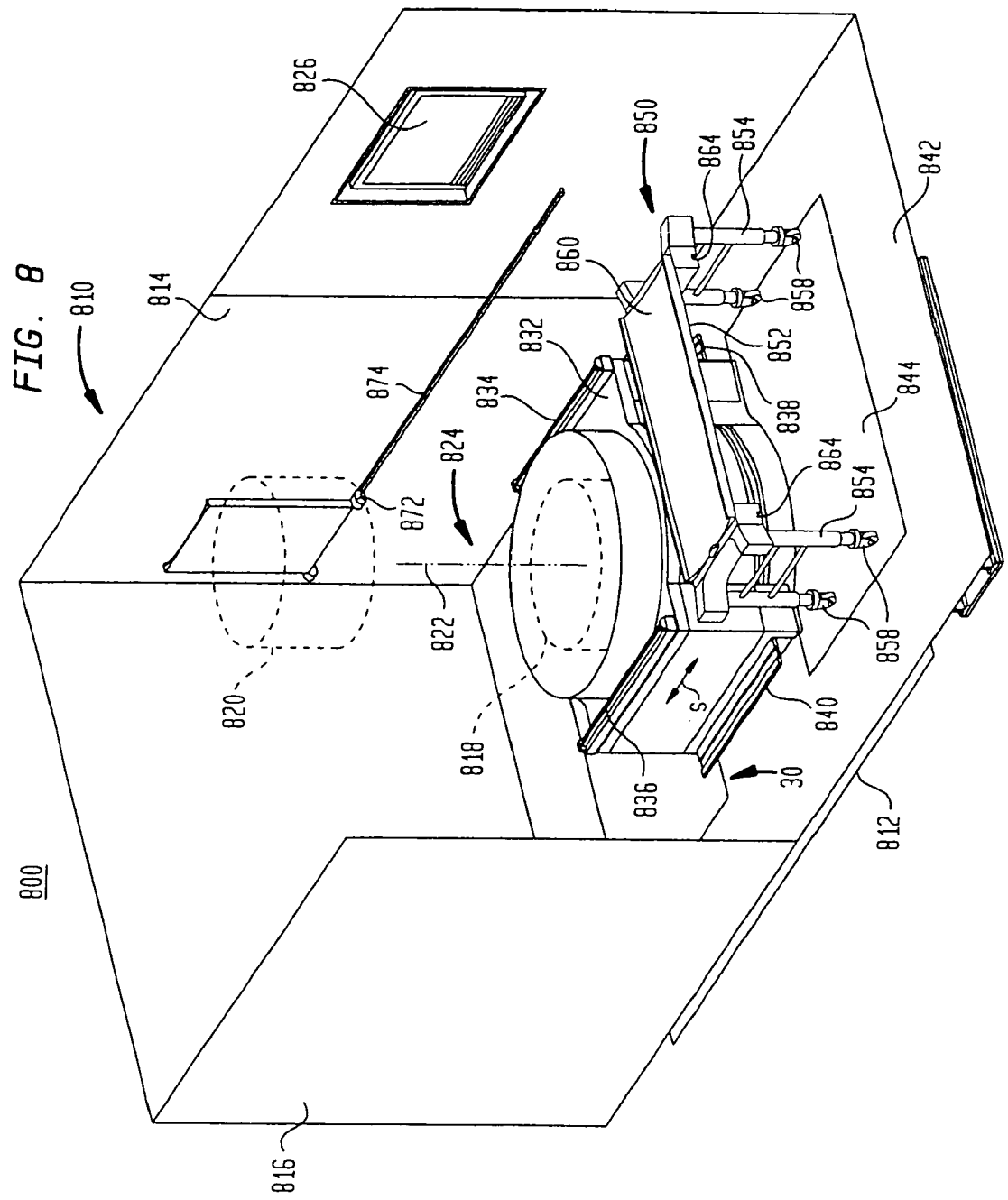
FIG. 8 is a schematic of a magnetic resonance imaging system in accordance with an aspect of the present invention.

Turning now to FIG. 8, there is shown an alternate system 800 in accordance with an additional aspect of the present invention. In contrast to the system discussed in relation to FIGS. 1 through 7, the system 800 features a different bed assembly and magnet structure but may also be equipped with the magnet previously described. As seen in FIG. 8, a magnet 810 as taught in the aforementioned patents, includes a ferromagnetic floor 812, a ferromagnetic ceiling (not shown) and a pair of ferromagnetic walls 814 and 816. Although walls 814 and 816 are shown schematically in FIG. 8 as planes, in fact, these walls have substantial thickness to provide adequate area for flux return. The magnet includes a lower pole structure 818 projecting upwardly from floor 812 and upper pole 820 structure, shown schematically in broken lines for clarity of illustration, projecting downwardly from the ceiling. The pole structures 818 and 820 are aligned with one another along a generally vertical pole axis 822 and define a patient-receiving space or gap 824 between them. The magnet incorporates a source of magnetic flux, such as one or more coils encircling one or both of the pole structures or other portions of the frame, which coils may be resistive or superconducting; or permanent magnet materials incorporated in the frame. The magnet provides a static field for magnetic resonance imaging. The MRI apparatus also includes conventional structures (not shown) such as a gradient coils for imposing magnetic field gradients within the patient-receiving space 824; RF transmitting and receiving apparatus for transmitting radio frequency signals into the patient-receiving space and receiving the resulting RF signals emitted by the patient's body, commonly referred to as magnetic resonance signals. As is conventional in the MRI art, the magnet also incorporates a computer (not shown) and appropriate interfacing devices, so that the computer can control operation of the gradient coils and RF coils and reconstruct a magnetic resonance image from the received magnetic resonance signals. A display 826 may be mounted within the room enclosed by the frame for displaying the images. As described in the aforementioned patents, a structure of this type defines a working space indicated schematically at 830 inside the frame sufficient to accommodate one or more medical personnel inside the frame, along with the patient.

In the apparatus according to one embodiment of the invention, a lower pole shroud 832 surrounds the lower pole structure 818 of the magnet. The lower pole shroud 832 is mounted to the magnet frame as, for example, to lower pole structure 818 or to a portion of the ferromagnetic floor 812 surrounding the lower pole structure, so that the lower pole shroud can be rotated around polar axis 822. For example, the lower pole shroud 832 can be supported by a large ball or roller bearing surrounding the lower pole structure 818. The lower pole shroud is equipped with a pair of slide supports 834 and 836 extending generally parallel to one another on opposite sides of polar axis 822. Each slide support is slidably mounted to the lower pole shroud 832 so that the slide support can be displaced in a slide direction indicated by arrow S in FIG. 8. A pair of retractable platforms 838 and 840 are provided on opposite sides of lower pole structure 818. In the extended position depicted in FIG. 8, platforms 838 and 840 project outwardly, away from the pole structure. With lower pole shroud 818 in the position shown in FIG. 8, platforms 838 and 840 extend generally parallel to the slide direction S. The magnet is equipped with a false floor 842 overlying the ferromagnetic floor 812. A portion 844 of the false floor is mounted on an elevating mechanism (not shown) so that the false floor can be moved between the flush position seen in FIG. 8, in which the portion 844 is flush with the remainder of floor 842, and the elevated position 844' shown in FIG. 9, in which the portion 844 is raised slightly above the rest of the false floor 842.

Figure 10:
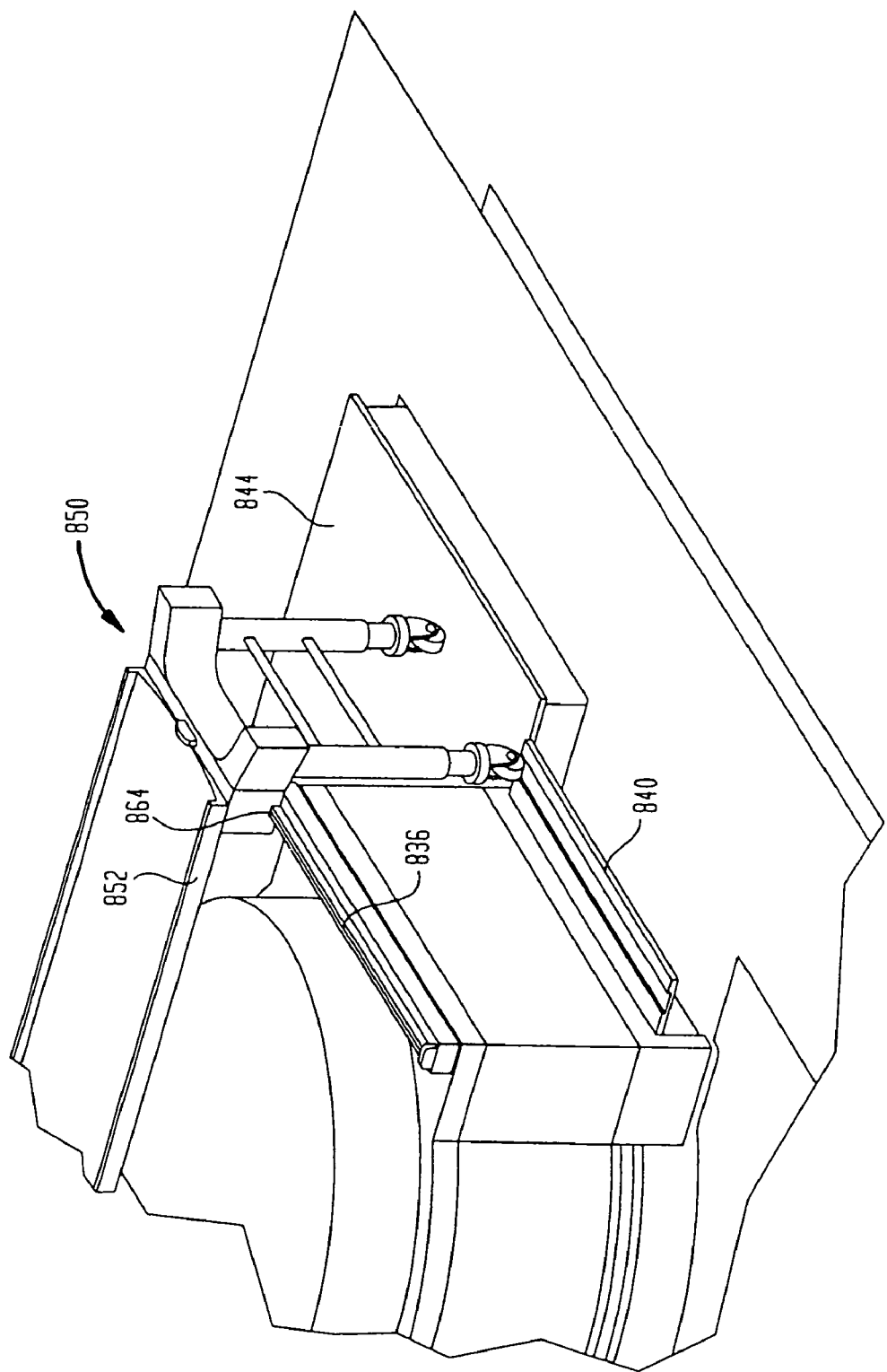
FIG. 10 is a schematic of a portion of the system of FIG. 8 in accordance with an aspect of the present invention.
Figure 16:
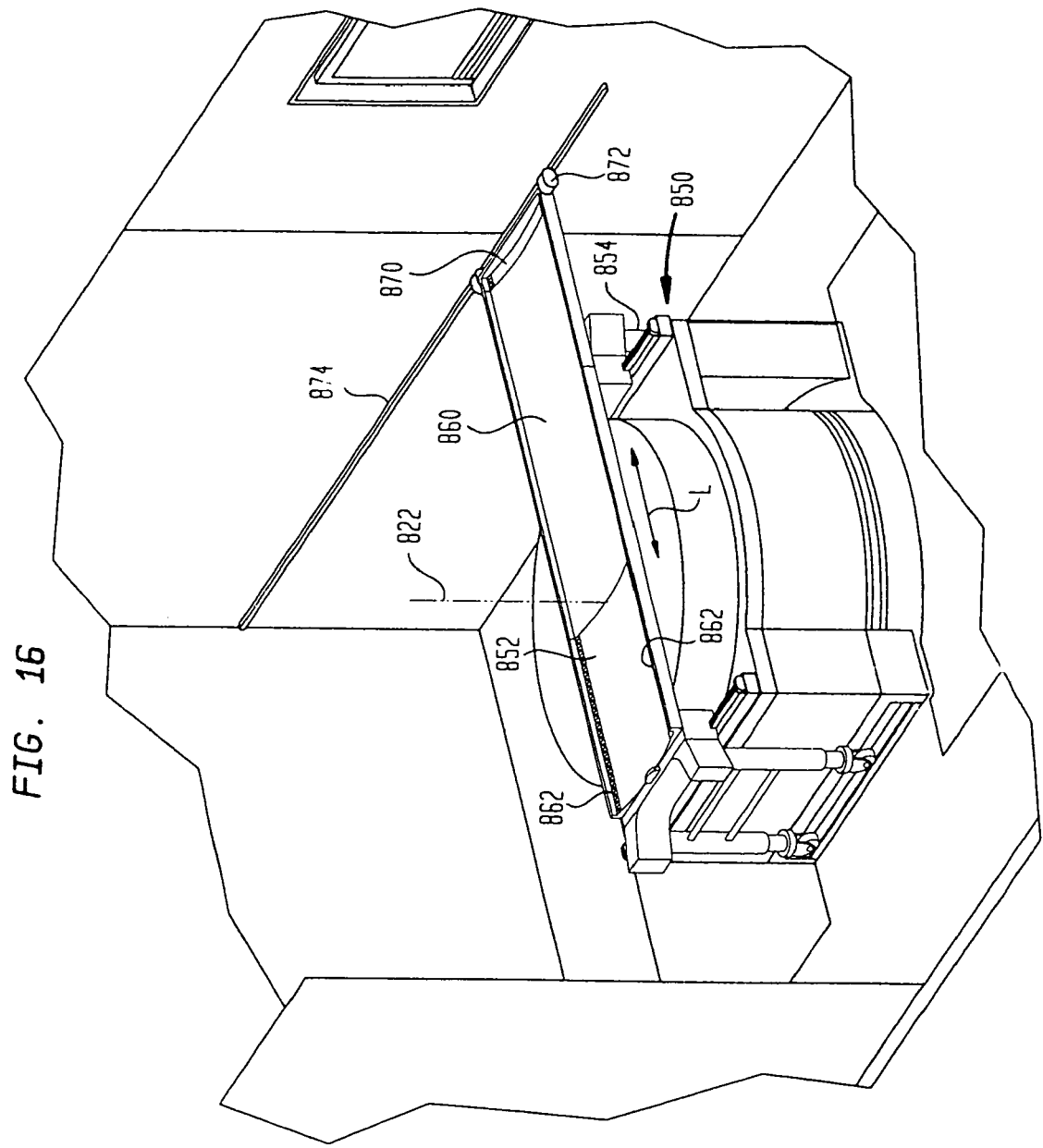
FIG. 16 is a schematic of the system of FIG. 15 in accordance with an aspect of the present invention.

A patient support 850 includes a chassis having a generally horizontal bridge portion 852 and a pair of end portions or leg portions 854 and 856 extending downwardly from the bridge portion. Each end portion is equipped with wheels 858. An elongated patient-supporting bed 860 overlies bridge portion 852 of the chassis. As best seen in FIG. 16, bridge portion 852, bed 860 or both are equipped with anti-friction bearings or other elements which allow bed 860 to slide in a lengthwise direction L relative to the bridge portion 852 of the chassis. As best seen in FIG. 10, the bridge portion is equipped with slots 864 on its underside adjacent end portions 854 and 856. These slots 864 are arranged to engage slides 834 and 836.

The magnet is further equipped with an auxiliary support element 870. This support element is mounted to a carrier 872 which, in turn, is supported on a rail 874 extending along one wall 814 of the magnet. In the retracted position seen in FIG.

Figure 13:
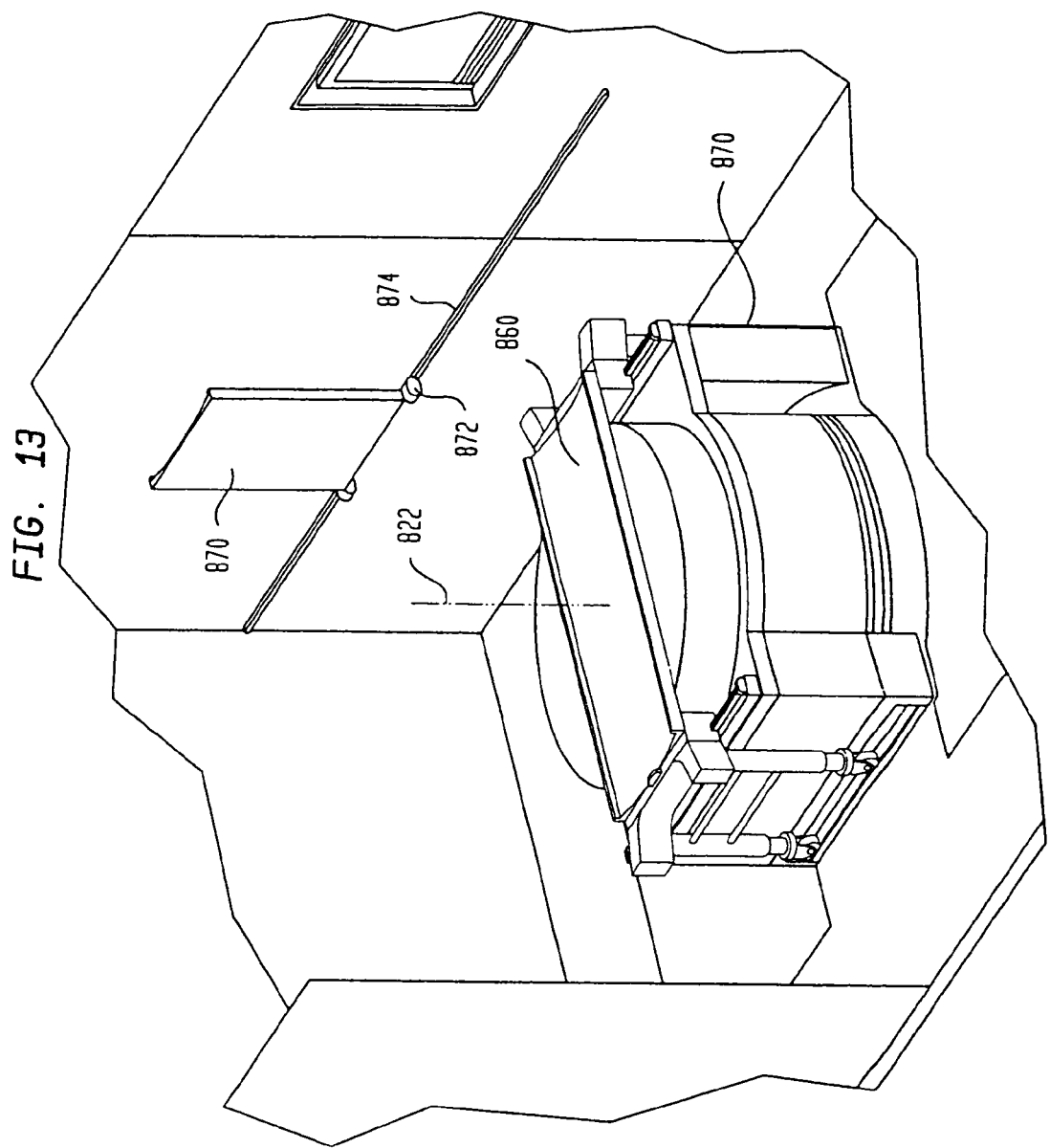
FIG. 13 illustrates a system in accordance with an aspect of the present invention.
Figure 14:
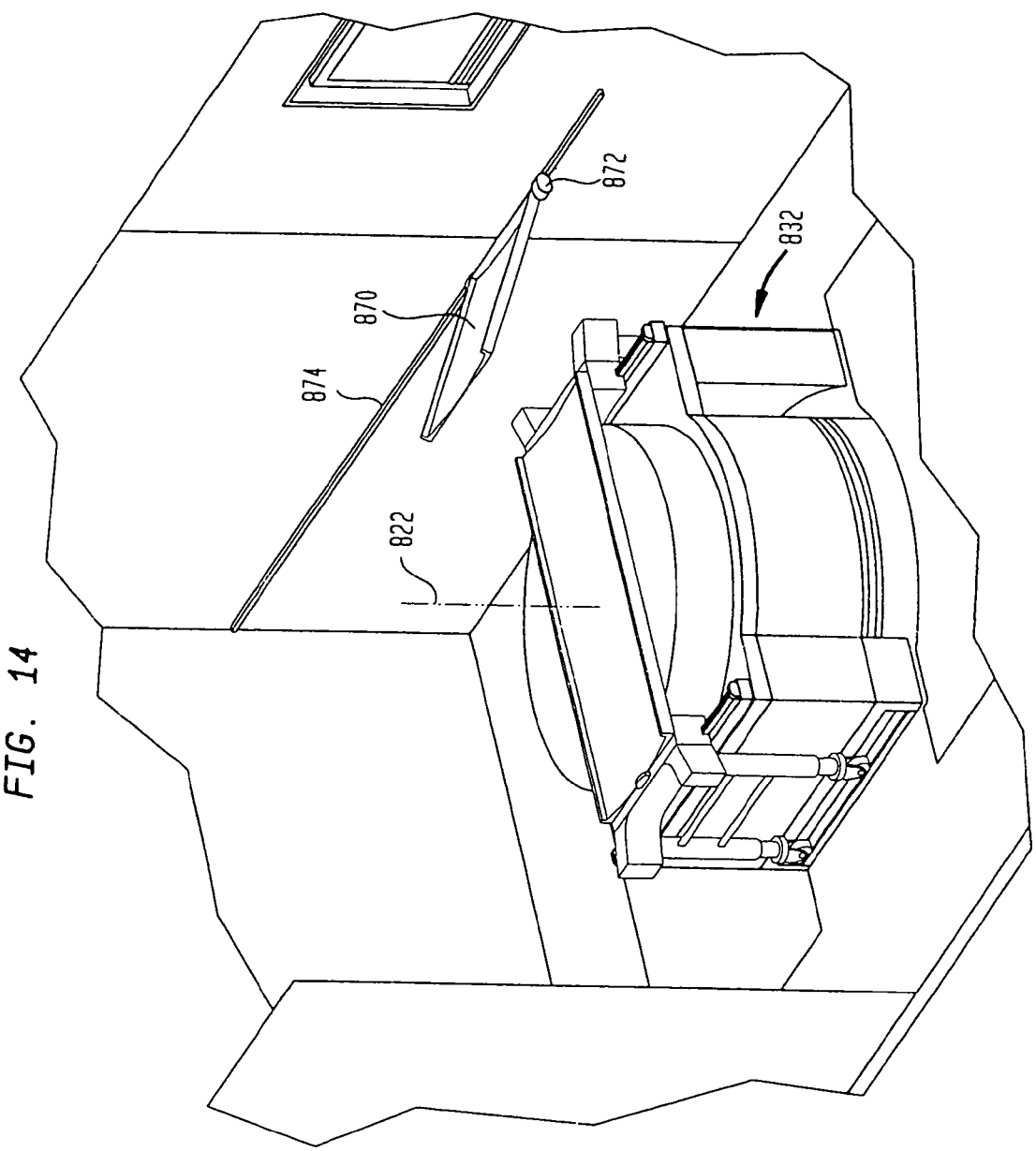
FIG. 14 is a schematic of the system of FIG. 13 in accordance with an aspect of the present invention.
Figure 15:
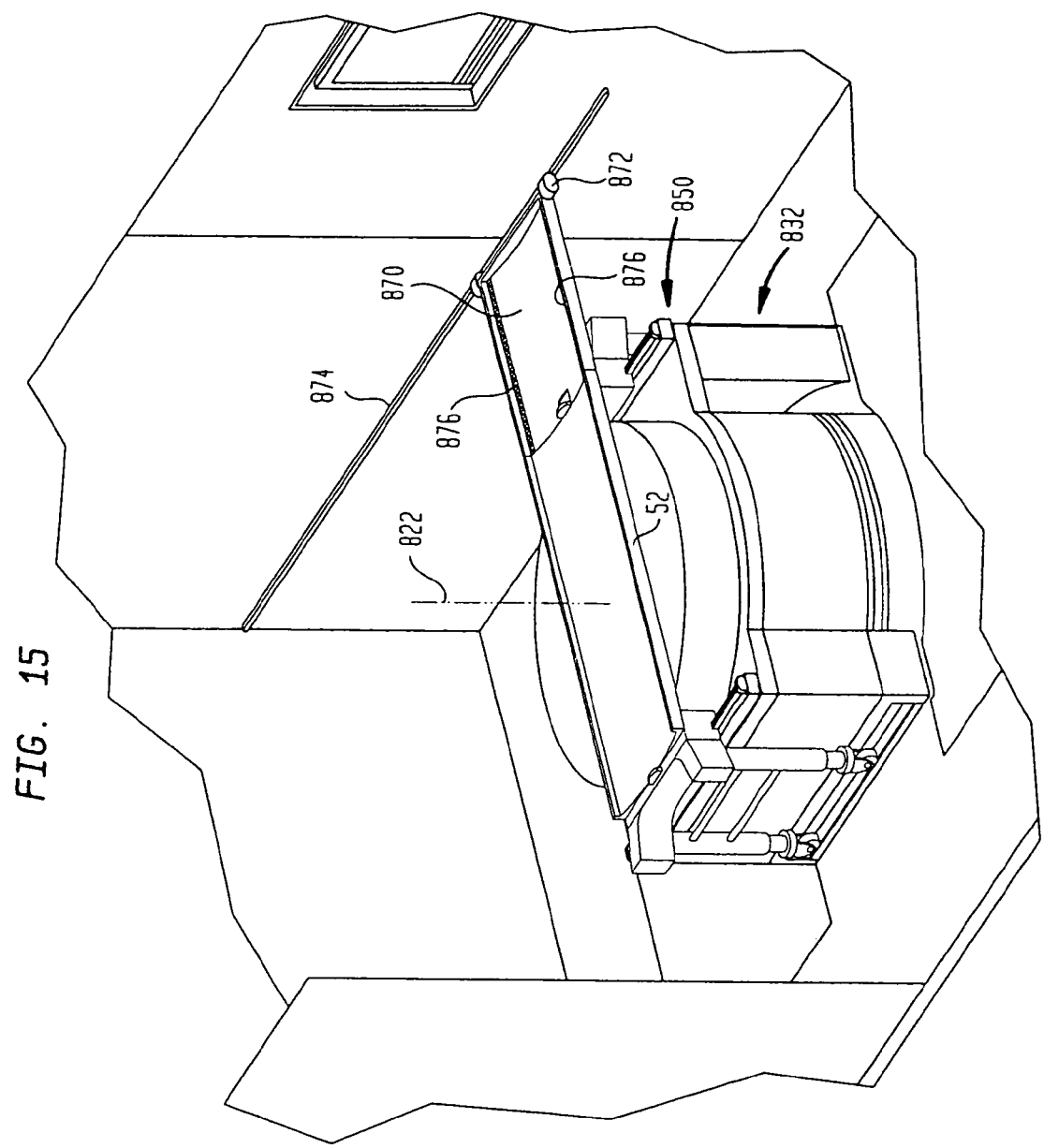
FIG. 15 illustrates a system in accordance with an aspect of the present invention.

8, auxiliary support 870 lies along wall 14, and hence, does not occupy appreciable space within the magnet. As best seen in FIGS. 13, 14 and 15, the auxiliary support 870 and carrier 872 can be moved along rail 874 to a position near pole axis 822 and lower pole shroud 832, and the auxiliary support can be tilted downwardly into a substantially horizontal position (FIG. 15) in which the end of the auxiliary support remote from carrier 872 rests on the chassis of support 850 in alignment with bridge portion 852. The auxiliary support 870 is equipped with anti-friction bearings 876 or other devices similar to those provided on the bridge portion 852 of the chassis.

Figure 9:
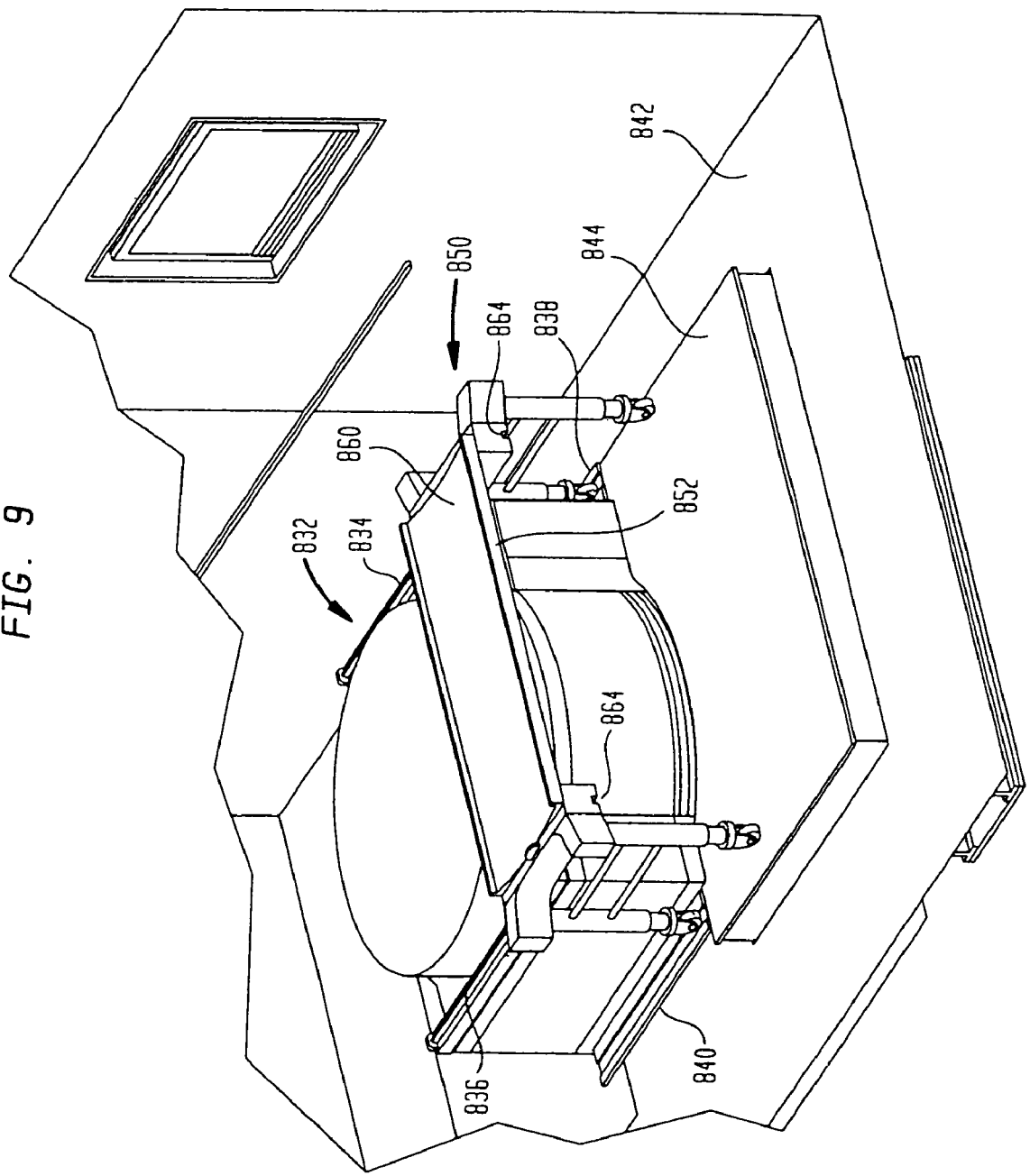
FIG. 9 is a schematic of a portion of the system of FIG. 8 in accordance with an aspect of the present invention.
Figure 11:
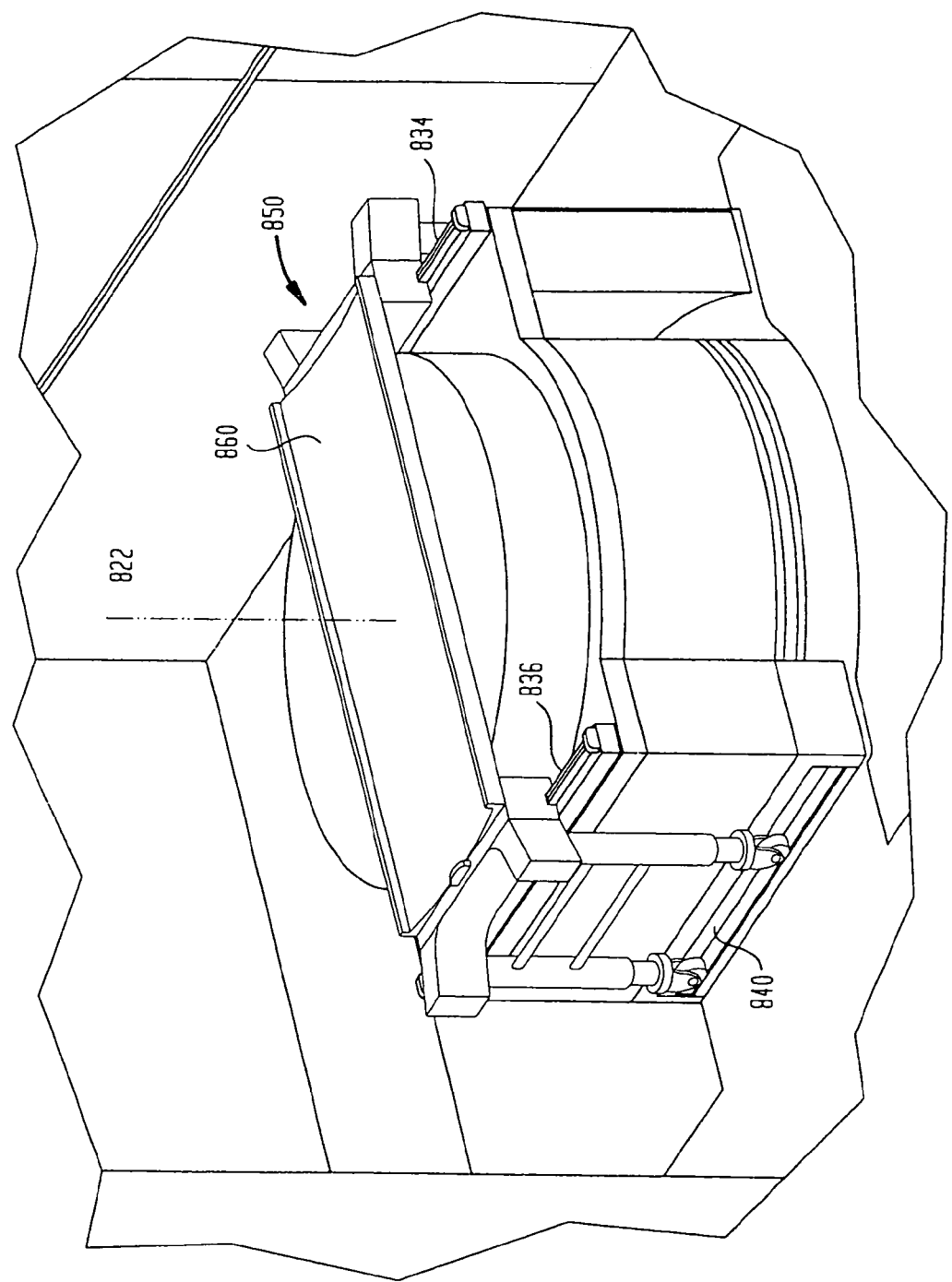
FIG. 11 illustrates a system in accordance with an aspect of the present invention.

In operation, a patient is loaded onto bed 860, and the patient support chassis 850 is wheeled across false floor 842 onto platform portion 844 and platforms 838 and 840 are placed in their extended position. As seen in FIG. 9, platform portion 844 is raised to its elevated position 844' so that the platform portion is flush with platforms 838 and 840. The patient support 850 is wheeled from the platform portion 44 onto the platforms 838 and 840 and engages slides 834 and 836 (FIGS. 9 and 10). The platforms 838 and 840 are retracted (FIG. 11), leaving the patient support 850 resting on slides 834 and 836. In this condition, the center of bed 60 is substantially centered with the polar axis 822. The patient can be imaged in this position. Moreover, medical personnel in working space 850 can perform surgical or other procedures on the patient.

Figure 12:
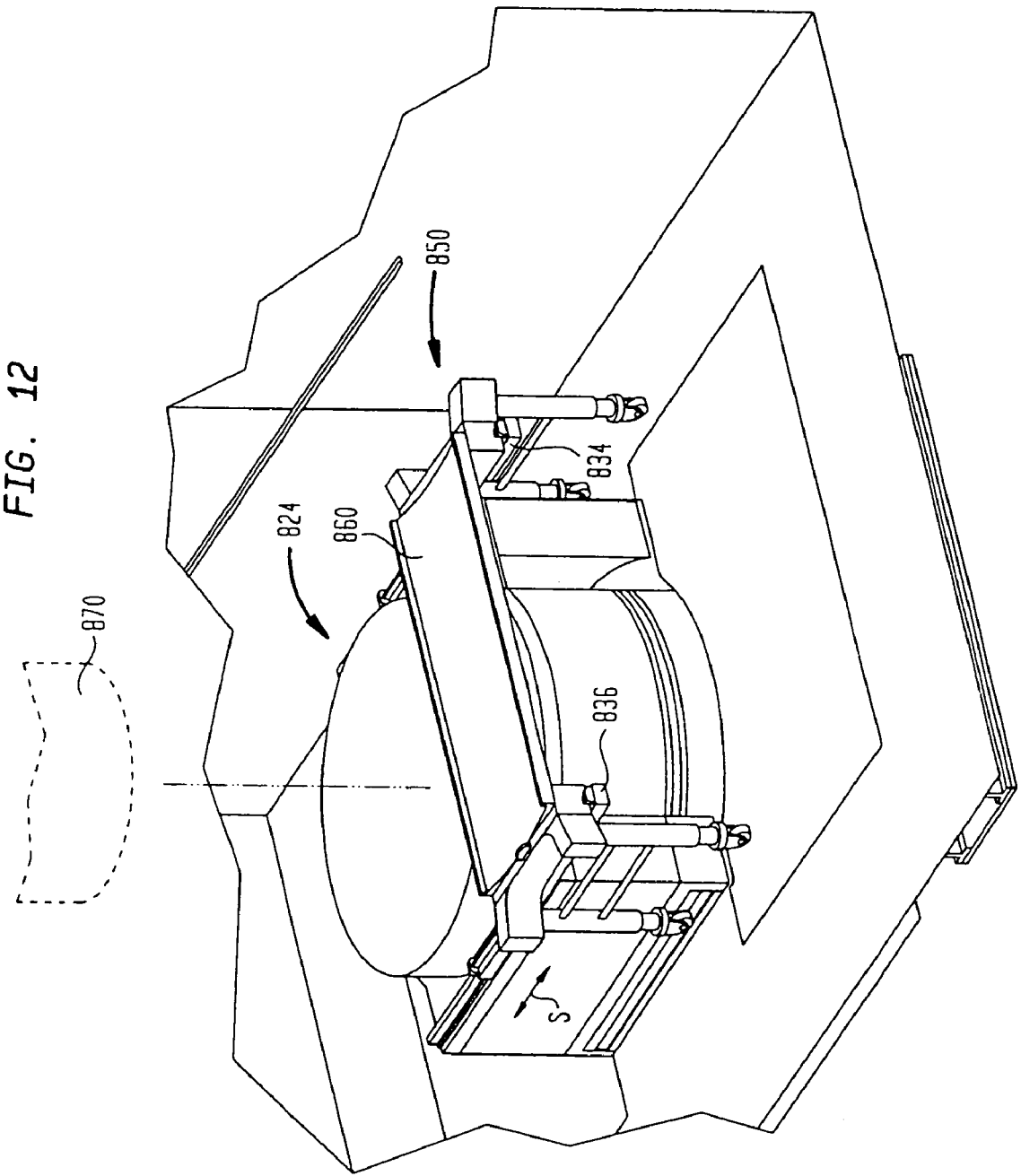
FIG. 12 is a schematic of the system of FIG. 11 in accordance with an aspect of the present invention.
Figure 18:
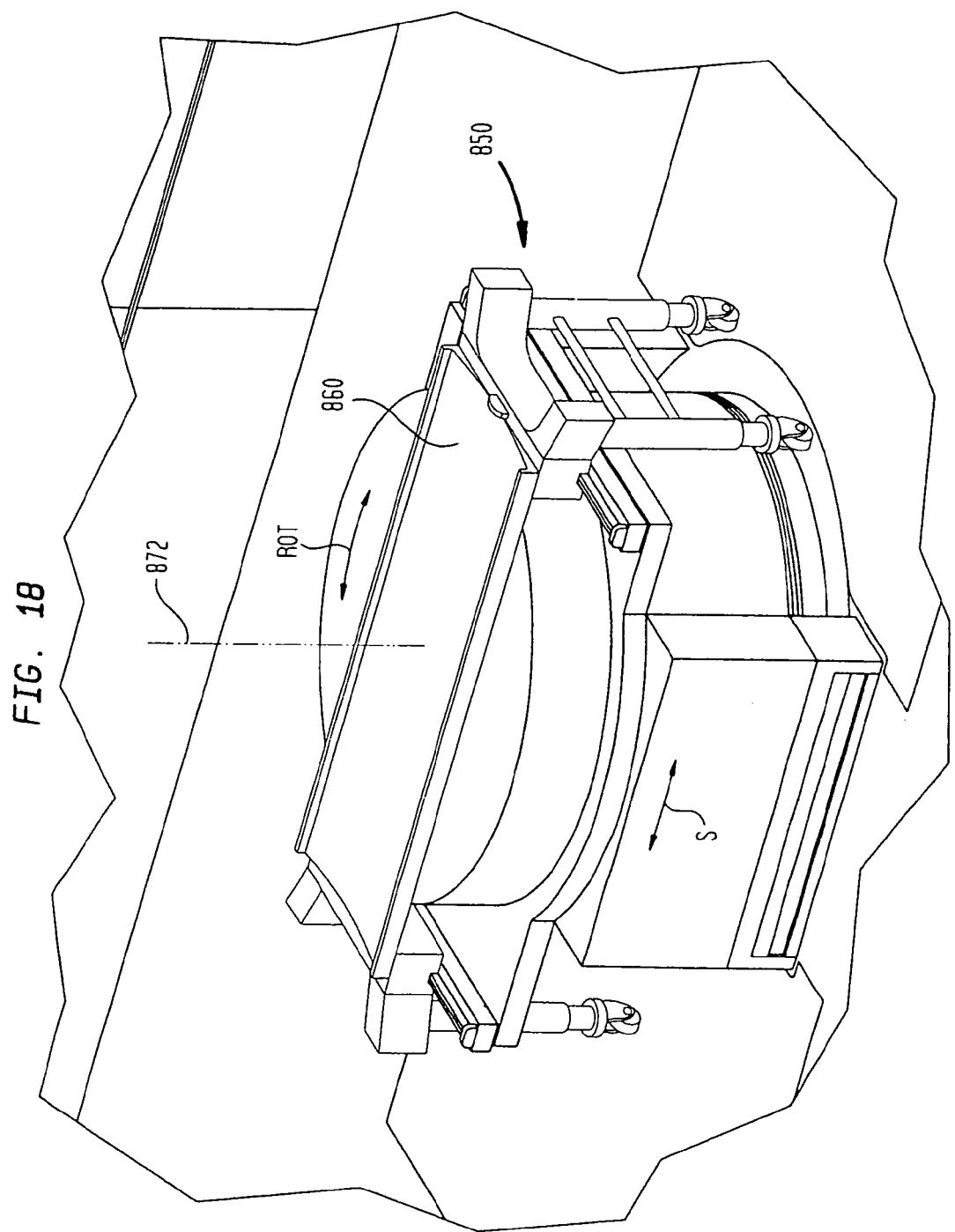
FIG. 18 illustrates a system in accordance with an aspect of the present invention.
Figure 19:
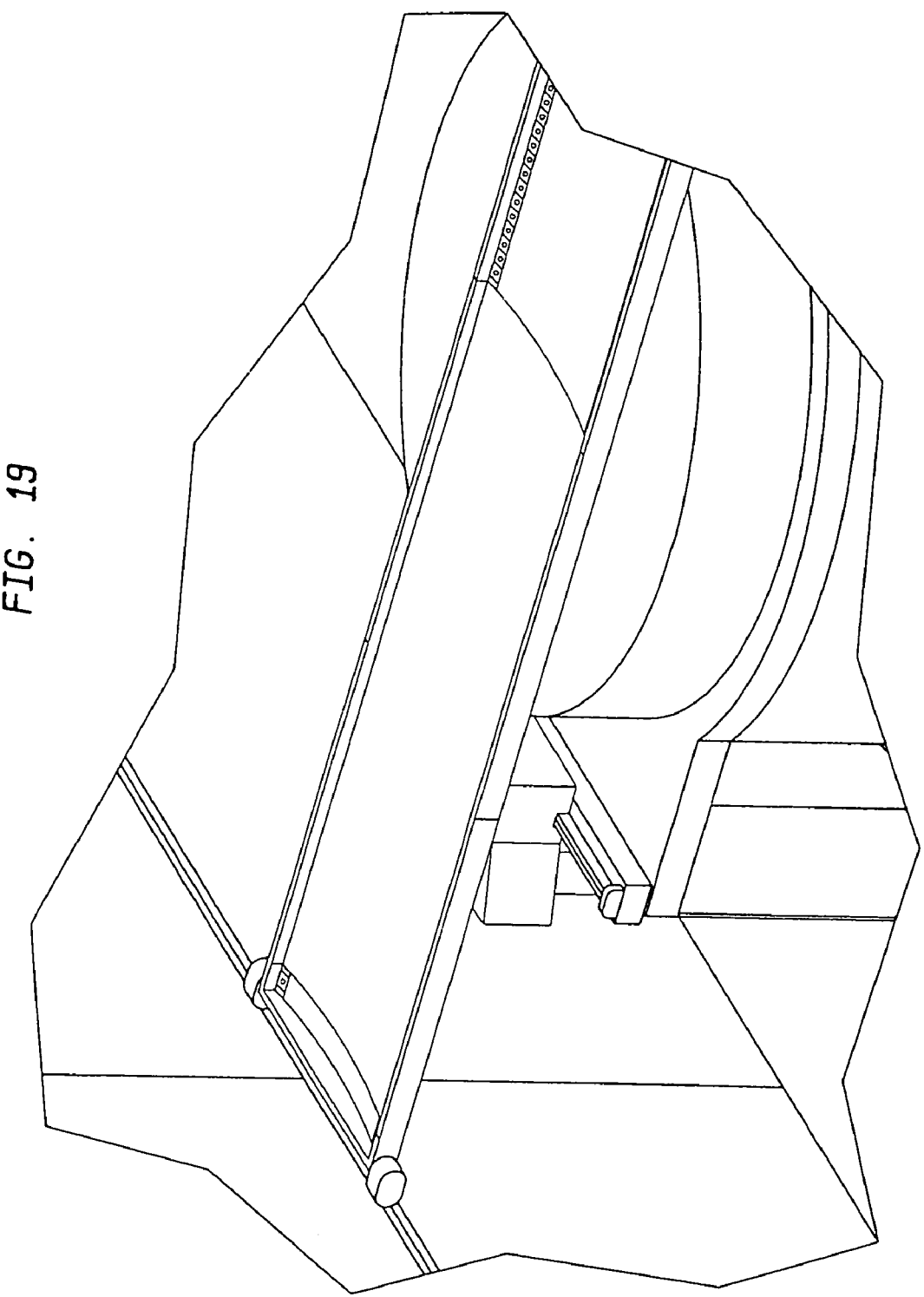
FIG. 19 is an exploded view of a system in accordance with an aspect of the present invention.
Figure 20:
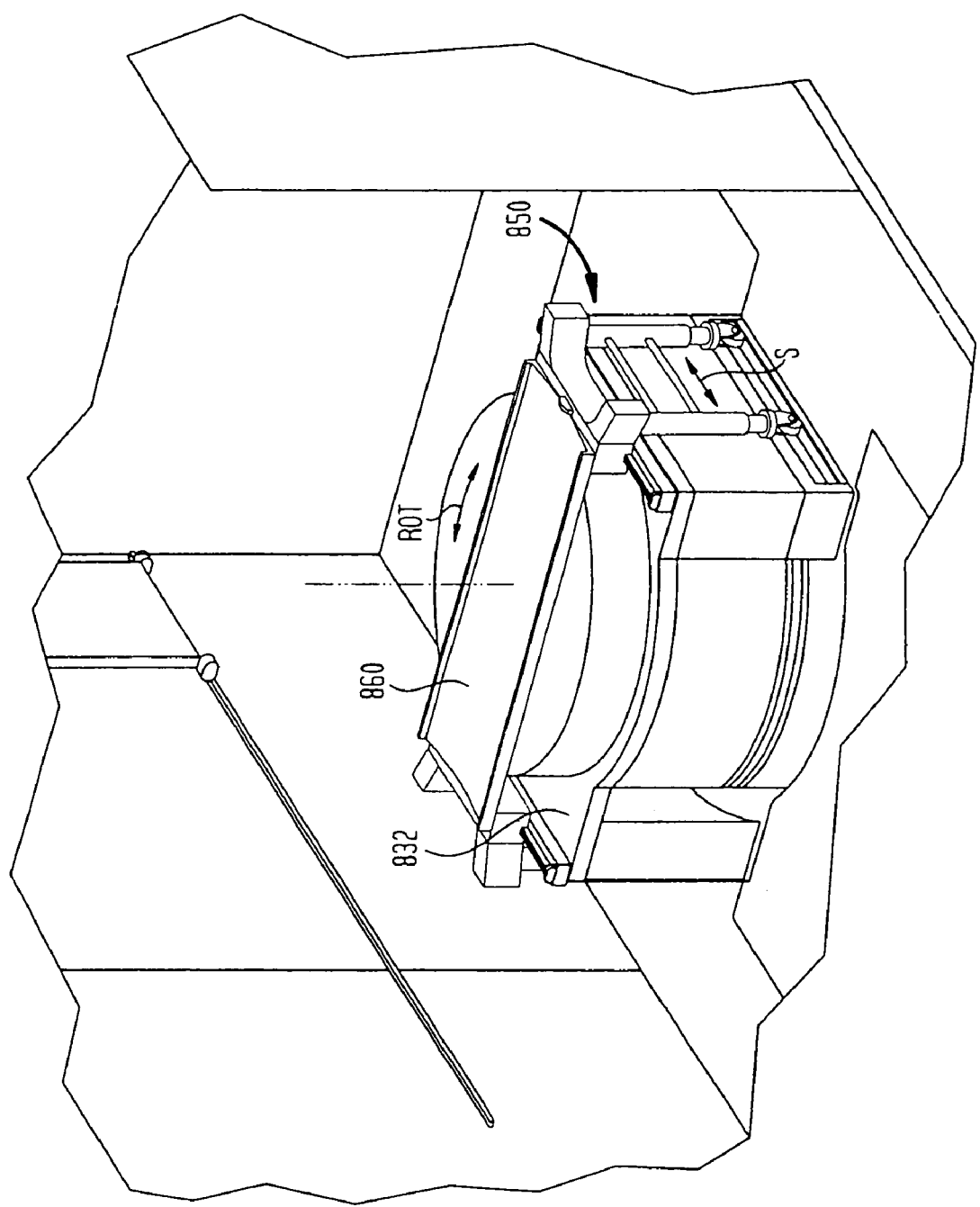
FIG. 20 is a perspective view of a magnetic resonance system in accordance with an aspect of the present invention.

As seen in FIG. 12, slides 834 and 836 can be extended to move the patient support 850 and bed 860 in slide direction S, so that the patient lies entirely outside of the patient-receiving space and does not lie beneath upper pole structure 820. This position provides maximum exposure of the patient for surgical or other procedures. As seen in FIGS. 18 and 19, the lower pole shroud 832 can be rotated around polar axis 22 between the position illustrated in FIG. 19 (the same position as shown in FIG. 8) and the position shown in FIG. 18, thereby rotating the patient support 850 and the bed 860 around the polar axis. This provides for repositioning the patient to a more convenient rotational position for surgery or other medical procedures.

Figure 17:
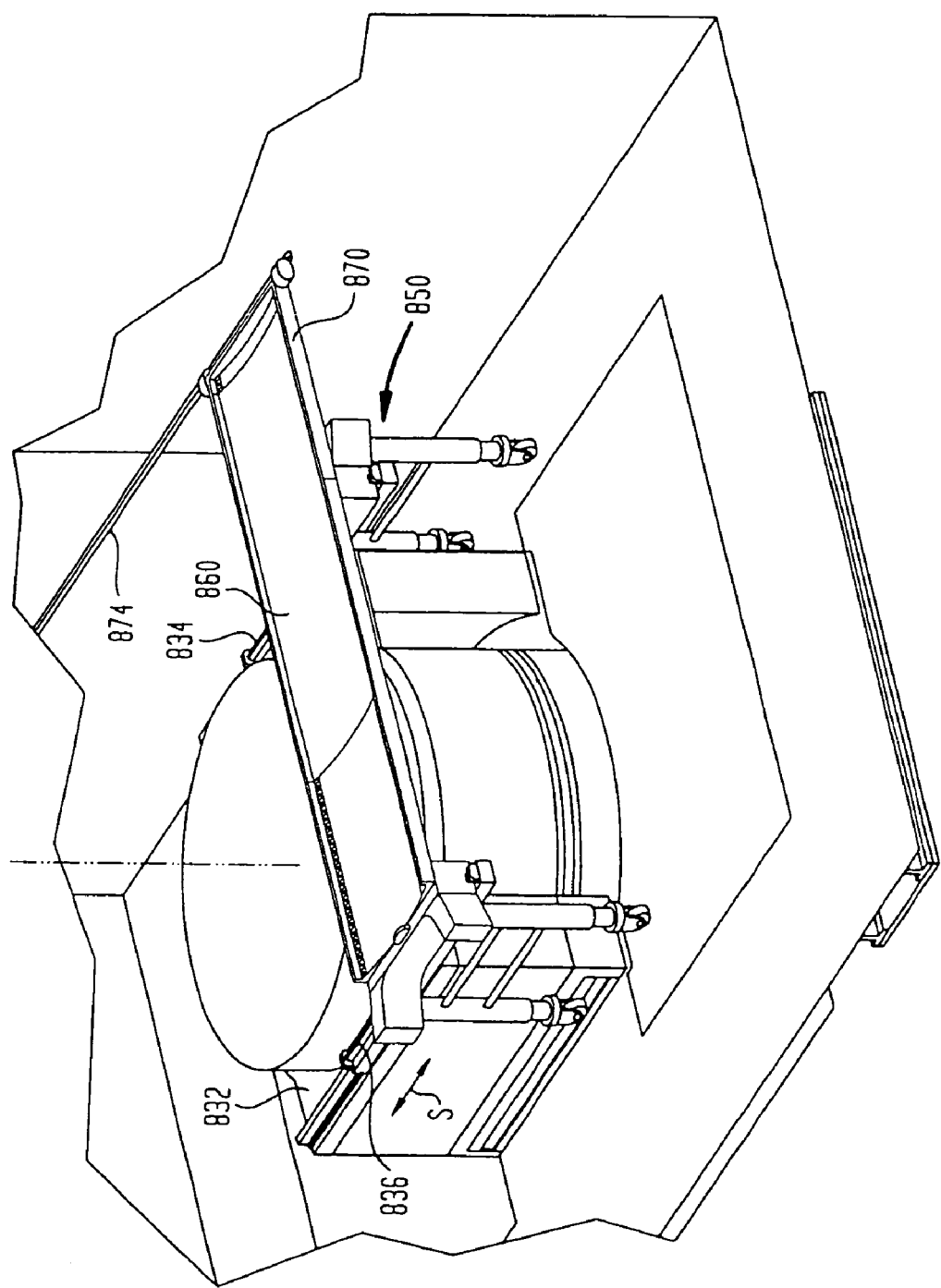
FIG. 17 is a schematic of the system of FIG. 15 in accordance with an aspect of the present invention.

As best appreciated with reference to FIGS. 14-16 in sequence, auxiliary support 870 can be positioned in its fully extended position, where it interlocks with support 850 (FIG. 15), and the bed 860 can be moved in lengthwise direction L so that a portion of bed 860 rests on the auxiliary support 870 and another portion of bed 860 is supported by the bridge portion 852 of the patient support chassis. This allows for substantial movement in direction L so that extreme portions of the patient's anatomy, as for example, the feet or the head, can be aligned with polar axis 822. Because a portion of the bed 60 is supported by the auxiliary support 870, the anti-friction bearings or other elements incorporated in the bed and in a patient support 50 need not provide all of the structural support. Stated another way, in the position illustrated in FIG. 16, bed 860 projects beyond chassis 850, but is not cantilevered. Instead, the projecting portion of the bed is supported on auxiliary support 870. As best seen in FIG. 17, when the bed 60 is supported in part on the auxiliary support 870, the auxiliary support 870 and carrier 872 can move along rail 874, along with the movement of chassis 850 and slides 834 and 836 in the slide direction S. Thus, even where the patient is in an extreme position, the patient can move out of the patient-receiving space for access.

Although only one auxiliary support 870 is depicted in the present drawings, the magnet may include two or more auxiliary supports disposed on two or more walls, so that the auxiliary supporting action can be provided in different rotational positions of the lower pole shroud 832. Also, the bed 860 can be moved slightly in directions L relative to chassis 850 without using the auxiliary support 870, as for example, where the lower pole shroud 832 is an intermediate rotational position. Because patient support 850 is supported on the lower pole shroud 832 during imaging and lower pole shroud 832, in turn, is supported on the ferromagnetic structure itself, vibrations or movement of false floor 840 will not affect imaging. Likewise, auxiliary support 870 is supported by a wall which is part of the ferromagnetic frame, and which is mechanically isolated from the false floor.

The components of the lower pole shroud 832, patient support 850, bed 860 and auxiliary support 870 desirably are formed from non-magnetic materials such as polymeric materials so that they do not interfere with the magnetic fields generated during use.

As mentioned above, the frames and poles of the magnets are preferably made with ferromagnetic materials. To achieve the field strengths at which the magnet is desired to operate, e.g., 6 Kilo-Gauss, it is further preferably to use low silicon steel that exhibits sufficiently high magnetic permeability in the polar regions. Low carbon steel is suitable and may be used in the frames. As magnet field strength increases pole saturation may place practical limits on the magnet design and place practical constraints on the size of the magnet poles, magnetic field strength and gap distance. The applicants have fabricated 3000 gauss magnets using grade 1008 steel. The applicants have found that grade 1006 steel is usable up to around 20,000 gauss and grade 1001 steel is usable up to around 22,000 gauss.

Numerous further variations and combinations of the features discussed above can be utilized without departing from the present invention. For example, the patient supports may be used with different magnets; the magnet need not include upper and lower projecting pole structures as shown. Also, with respect to the embodiments shown and discussed with respect to FIGS. 8 through 20, the end portions 854 and 856 of the patient support chassis may be arranged to extend and retract, and thereby raise and lower bridge portion 852 and bed 860. In such a variant, the platform portion 844 of the false floor may be stationary, and the platforms 838 and 840, discussed above, may be omitted. The patient support 50 may be positioned on slides 834 and 836 by rolling the patient support across the false floor, whereupon the end portions 854 and 856 of the chassis may be retracted so as to leave the chassis supported on the slides. Also, auxiliary support 870 may be replaced or supplemented by an arm, cable or strut extending from the ceiling element of the ferromagnetic frame.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A magnetic resonance imaging system, comprising:
   a ferromagnetic frame that is operative to support an upper pole member and a lower pole member along a vertical polar axis such that a gap is defined between the upper and lower pole members, the frame being mounted to a well that includes a pair of support columns that project parallel to the polar axis so as to define a well floor between them; and an access floor for providing access to the gap located above the well floor, the access floor being isolated from the ferromagnetic frame and pole members.

2. The system of claim 1, wherein the ferromagnetic frame is mounted to the well support columns by a pair of trusses, each truss being supported on one or more air bags.

3. The system of claim 1, wherein the access floor comprises a floor plate mounted to a floor frame, the floor frame being supported by the well floor.

4. The system of claim 1, wherein the access floor further includes an opening that includes a platform that may be elevated or lowered in a direction parallel to the polar axis and relative to the access floor.

5. The system of claim 1, further comprising a sensor system for detecting the presence of an object on the platform.

6. A patient positioning system for a magnetic resonance imaging magnet, comprising:
 a ferromagnetic frame that is operative to support an upper pole and a lower pole along a vertical polar axis such that a gap is defined between the upper and lower poles;
 a support frame mounted to the lower pole, the support frame including a pair of support beams extending parallel to each other on opposite sides of the lower pole; and
 a bed having a frame and a slab, the bed being mounted to the support frame such that each of the support beams engages the frame of the bed.

7. The system of claim 6, wherein the lower pole extends circularly around the polar axis and the support frame is rotatable around the lower pole.

8. The system of claim 7, wherein the beams are operable to move the bed over the surface of the pole.

9. The system of claim 8, wherein the bed slab is operable to cantilever relative to the lower pole.

10. The system of claim 9, wherein the frame defines a workspace that can provide access to surgeon to perform MRI guided intervention.

* * * * *